United States Patent
Bell et al.

(10) Patent No.: US 10,227,433 B2
(45) Date of Patent: Mar. 12, 2019

(54) CYCLOALKYLNORBORNENE MONOMERS, POLYMERS DERIVED THEREFROM AND THEIR USE IN PERVAPORATION

(71) Applicant: PROMERUS, LLC, Brecksville, OH (US)

(72) Inventors: Andrew Bell, Lakewood, OH (US); Leah Langsdorf, Akron, OH (US); Oleksandr Burtovyy, Brecksville, OH (US)

(73) Assignee: PROMERUS, LLC, Brecksville, OH (US)

( * ) Notice: Subject to any disclaimer, the term of this patent is extended or adjusted under 35 U.S.C. 154(b) by 317 days.

(21) Appl. No.: 15/257,634

(22) Filed: Sep. 6, 2016

(65) Prior Publication Data

US 2016/0369026 A1 Dec. 22, 2016

Related U.S. Application Data

(62) Division of application No. 13/959,873, filed on Aug. 6, 2013, now Pat. No. 9,468,890.

(Continued)

(51) Int. Cl.
*B01D 61/36* (2006.01)
*B01D 67/00* (2006.01)
(Continued)

(52) U.S. Cl.
CPC .......... *C08F 232/08* (2013.01); *B01D 61/362* (2013.01); *B01D 67/0009* (2013.01);
(Continued)

(58) Field of Classification Search
CPC ..... C08F 232/08; Y02E 50/17; B01D 61/362; B01D 67/009; B01D 69/02; B01D 69/08; B01D 69/12; B01D 71/26; B01D 72/44; B01D 71/76; B01D 2235/20; C07C 13/40; C07C 13/42; C07C 13/47; C07C 13/50; C07C 13/54; C07C 13/547; C07C 13/573; C07C 13/605; C07C 13/61; C07C 13/615;
(Continued)

(56) References Cited

U.S. PATENT DOCUMENTS 3,330,815 A 7/1967 McKeon et al.
5,087,677 A 2/1992 Brekner et al.
(Continued)

FOREIGN PATENT DOCUMENTS

EP 0608903 8/1994
EP 1878488 1/2008

OTHER PUBLICATIONS

B. De Clercq and F. Verpoort, "Assessing the Scope of the Introduction of Schiff Bases as Co-Ligands for Monometallic and Homobimetallic Ruthenium Ring-Opening Metathesis Polymerisation and Ring-Closing Metathesis Initiators", Adv. Synth. Catal. 2002, 344, 639-648 (Year: 2002).*

(Continued)

*Primary Examiner* — James C Goloboy
(74) *Attorney, Agent, or Firm* — Balaram Gupta

(57) ABSTRACT

A variety of polycycloalkyl polynorbornene monomers and polymers derived therefrom are disclosed and claimed. The polymers and copolymers as disclosed herein are useful for forming pervaporation membranes, among other uses.

13 Claims, 4 Drawing Sheets

Related U.S. Application Data

(60) Provisional application No. 61/680,439, filed on Aug. 7, 2012, provisional application No. 61/781,437, filed on Mar. 14, 2013.

(51) Int. Cl.

| | | |
|---|---|---|
| *B01D 69/02* | (2006.01) | |
| *B01D 69/08* | (2006.01) | |
| *B01D 69/12* | (2006.01) | |
| *B01D 71/26* | (2006.01) | |
| *B01D 71/44* | (2006.01) | |
| *B01D 71/76* | (2006.01) | |
| *C07C 13/40* | (2006.01) | |
| *C07C 13/42* | (2006.01) | |
| *C07C 13/47* | (2006.01) | |
| *C07C 13/50* | (2006.01) | |
| *C07C 13/54* | (2006.01) | |
| *C07C 13/61* | (2006.01) | |
| *C07C 13/64* | (2006.01) | |
| *C07C 13/68* | (2006.01) | |
| *C07C 29/76* | (2006.01) | |
| *C07C 31/12* | (2006.01) | |
| *C07C 37/82* | (2006.01) | |
| *C07C 39/04* | (2006.01) | |
| *C08F 232/08* | (2006.01) | |
| *C07C 13/465* | (2006.01) | |
| *C07C 13/547* | (2006.01) | |
| *C07C 13/573* | (2006.01) | |
| *C07C 13/605* | (2006.01) | |
| *C07C 13/615* | (2006.01) | |

(52) U.S. Cl.
CPC ............ *B01D 69/02* (2013.01); *B01D 69/08* (2013.01); *B01D 69/12* (2013.01); *B01D 71/44* (2013.01); *B01D 71/76* (2013.01); *C07C 13/40* (2013.01); *C07C 13/42* (2013.01); *C07C 13/465* (2013.01); *C07C 13/47* (2013.01); *C07C 13/50* (2013.01); *C07C 13/54* (2013.01); *C07C 13/547* (2013.01); *C07C 13/573* (2013.01); *C07C 13/605* (2013.01); *C07C 13/61* (2013.01); *C07C 13/615* (2013.01); *C07C 13/64* (2013.01); *C07C 13/68* (2013.01); *C07C 29/76* (2013.01); *C07C 37/82* (2013.01); *B01D 71/26* (2013.01); *B01D 2325/20* (2013.01); *C07C 2602/42* (2017.05); *C07C 2603/10* (2017.05); *C07C 2603/28* (2017.05); *C07C 2603/62* (2017.05); *C07C 2603/64* (2017.05); *C07C 2603/66* (2017.05); *C07C 2603/74* (2017.05); *C07C 2603/90* (2017.05); *C07C 2603/91* (2017.05); *Y02E 50/17* (2013.01)

(58) Field of Classification Search
CPC ......... C07C 13/64; C07C 13/68; C07C 29/76; C07C 37/82; C07C 2602/42; C07C 2603/10; C07C 2603/28; C07C 2603/62; C07C 2603/64; C07C 2603/66; C07C 2603/74; C07C 2603/90; C07C 2603/91
See application file for complete search history.

(56) References Cited

U.S. PATENT DOCUMENTS

| | | |
|---|---|---|
| 5,344,900 A | 9/1994 | Maezawa et al. |
| 5,468,819 A | 11/1995 | Goodall et al. |
| 5,677,407 A | 10/1997 | Sojka |
| 5,741,869 A | 4/1998 | Goodall et al. |
| 5,929,181 A | 7/1999 | Makovetsky et al. |
| 6,136,499 A | 10/2000 | Goodall et al. |
| 6,310,160 B1 | 10/2001 | Kodemura |
| 6,455,650 B1 | 9/2002 | Lipian et al. |
| 6,713,154 B1 | 3/2004 | Tsunogae et al. |
| 6,825,307 B2 | 11/2004 | Goodall |
| 7,101,654 B2 | 9/2006 | Wu et al. |
| 8,079,480 B2 | 12/2011 | Haring et al. |
| 8,470,944 B2 | 6/2013 | Knapp et al. |
| 9,328,791 B2 | 5/2016 | Nakajima |
| 2002/0088748 A1 | 7/2002 | Allcock et al. |
| 2009/0188863 A1* | 7/2009 | Knapp ................. B01D 61/362 210/640 |
| 2009/0270247 A1 | 10/2009 | Rhodes et al. |
| 2014/0042090 A1 | 2/2014 | Bell et al. |

OTHER PUBLICATIONS

STIC structure search for the compound of formula (III).*
Bob De Clerq, et al., "Assessing the Scope of the Introduction of Schiff Bases as Co-Ligands for Monometallic and Homobimetallic Ruthenium Ring-Opening Metathesis Polymerisation and Ring-Closing Metathesis Initiators," Advanced Synthesis & Catalysis, pp. 639-648, vol. 344, Issue 6-7, Aug. 2002.
Maria Angeles Sarmentero et al, Catalytic Hydrogenation of Norbornadiene by a Rhodium Complex in a Self-Folding Cavitand, Angew. Chem. Int. Ed., Oct. 4, 2010, 7489-7492, vol. 49.
International Search Report dated Jan. 22, 2014 for PCT/US2013/053724 filed Aug. 6, 2013.
Written Opinion of the International Searching Authority dated Jan. 22, 2014 for PCT/US2013/053724 filed Aug. 6, 2013.

* cited by examiner

CYCLOALKYLNORBORNENE MONOMERS, POLYMERS DERIVED THEREFROM AND THEIR USE IN PERVAPORATION

CROSS REFERENCE TO RELATED APPLICATIONS

This application is a divisional of U.S. application Ser. No. 13/959,873, filed Aug. 6, 2013, now allowed, which claims the benefit of U.S. Provisional Application No. 61/680,439, filed Aug. 7, 2012 and the benefit of U.S. Provisional Application No. 61/781,437, filed Mar. 14, 2013, all of which are incorporated herein by reference in their entirety.

TECHNICAL FIELD

The present invention relates generally to a series of cycloalkyl and polycycloalkyl norbornene monomers and polymers derived therefrom which are suitable for use as pervaporation membrane films and more specifically the composition and preparation of such monomers, polymers, membrane films made from such polymers and the use of such membrane films for pervaporation processes.

BRIEF DESCRIPTION OF THE DRAWINGS

Embodiments in accordance with the present invention are described below with reference to the following accompanying figures and/or images. Where drawings are provided, it will be drawings which are simplified portions of various embodiments of this invention and are provided for illustrative purposes only.

DETAILED DESCRIPTION

Figure 1:
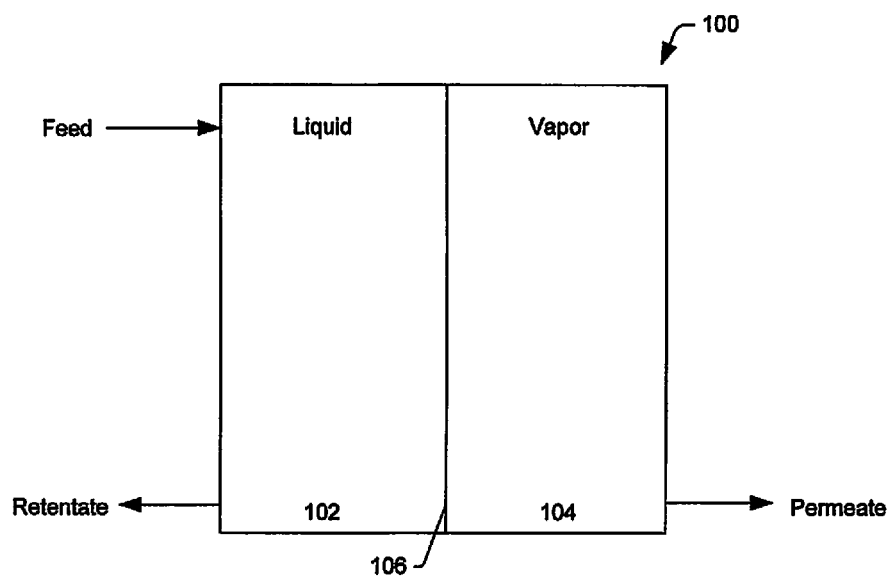
FIG. 1 depicts a pervaporation module in accordance with embodiments of the invention.

With the increased interest in producing biological fuel, such as ethanol, butanol, and the like, there is a heightened interest in developing environmentally friendly separation processes that economically separate organic materials from water. There is also growing need for purification of water stream contaminated by an industrial process as well as to the isolation of an organic product from an aqueous fermentation broth designed to form various organic solvents via a biological process, for example, phenol from the broth of a fermentation reactor or any other biologically formed broth, e.g., an algae broth. Also, there is a growing interest in separating value-added products from biological and industrial waste including any biomass-derived waste. While it is well known to use processes such as distillation and gas stripping to effect such separations, these conventional processes, particularly distillation, are generally characterized by high capital and energy costs thus often making such conventional processes problematic, for example, it has been noted that in excess of 60% of the heating value of a biofuel such as butanol can be "wasted" if conventional separation processes are employed.

Even more importantly the organic products, particularly, the organic solvents that are either made by the above noted bio-processes or extracted from organic wastes are gaining more and more industrial applications. For instance, about half of the n-butanol produced and its esters (e.g., n-butyl acetate) are used as solvents in the coatings industry, including as solvents for dyes, e.g., printing inks. Other well known applications of butyl esters of dicarboxylic acids, phthalic anhydride and acrylic acid include as plasticizers, rubber additives, dispersants, semisynthetic lubricants, additives in polishes and cleaners, e.g., floor cleaners and stain removers, and as hydraulic fluids. Butanol and its esters are also used as solvents, including as extractants in the production of drugs and natural products, such as antibiotics, hormones, vitamins, alkaloids and camphor. Various other uses of butanol and its esters and ethers include as solubilizer in the textile industry, e.g., as additive in spinning baths or as carrier for coloring plastics, as additives in de-icing fluids, additive in gasoline for spark-ignition engines, as feedstock for the production of glycol ethers, among various other uses.

Therefore, an alternate process for effecting such separations known as pervaporation has received considerable attention as a solution to the aforementioned "waste". In a pervaporation process, a charge liquid, typically a mixture of two or more liquids, such as a fermentation broth, is brought into contact with a membrane film having the property to allow one component of the charge liquid to preferentially permeate the membrane. This permeate is then removed as a vapor from the downstream side of the membrane film, generally by applying vacuum on the permeate side of the membrane. Particularly, pervaporation process has proven to be a method of choice in the separation of liquid mixtures having similar volatilities, such as azeotropic mixtures that are difficult to separate by conventional methods. While polymers such as polyimides, polyether-polyamide, polydimethylsiloxanes and the like have been used to form pervaporation membranes with some success, none have demonstrated thus far the necessary characteristics needed for a commercially viable membrane material. For example, pervaporation membranes, such as PERVAP 1060 (made from poly(dimethylsiloxane), PDMS), PERVAP 1070 (made from zeolite, ZSM-5, filled PDMS) (Sulzer Chemtech Membrane Systems A.G., Neunkirchen, Germany) and PEBA (block copolymer polyether-polyamide, GKSS-Forschungszentrum Geesthacht GmbH, Geesthacht, Germany) are available for the separation of various low volatile organics from aqueous mixtures. However, there is still a need to develop membranes having better performance, which can provide efficient separation of organics from aqueous mixtures at lower capital and reduced operating cost.

Disclosed herein are embodiments in accordance with the present invention that encompass monomers, polymer composition embodiments, film and film composite embodiments and pervaporation membrane embodiments formed therefrom that advantageously provide hitherto unachievable separation of organics from a variety of mixtures including fermentation broth, industrial waste, among others.

Exemplary embodiments of the present invention will be described hereinbelow. Various modifications, adaptations or variations of such exemplary embodiments may become apparent to those skilled in the art as such are disclosed. It will be understood that all such modifications, adaptations or variations that rely upon the teachings of the present invention, and through which these teachings have advanced the art, are considered to be within the scope and spirit of the present invention. For example, while the exemplary embodiments described herein generally reference the separation of butanol and/or phenol from an aqueous charge liquid, such are not meant to limit the present invention only to embodiments for butanol and/or phenol separation. Thus some embodiments of the present invention encompass the separation of any organic material from an aqueous based charge liquid where an appropriate polynorbornene pervaporation membrane can be formed. For example, some embodiments encompass the separation of a hydrophobic organic material from a hydrophilic charge liquid using an appropriate polynorbornene pervaporation membrane. Still other embodiments of the present invention encompass separation of non-polar and polar organic materials. Examples of such separations include, but are not limited to, aromatics such as benzene or toluene from water miscible alcohols such as methanol or ethanol and the separation of non-polar hydrocarbyl-based materials such as hexanes and heptanes from polar heterocarbyl-based materials. Various other organics also include volatile organic solvents, such as tetrahydrofuran (THF), ethyl acetate (EA), acetone, methyl ethyl ketone (MEK), methyl isobutyl ketone (MIBK), and the like, all of which can be present either in a fermentation broth or in an industrial waste.

In addition, unless otherwise indicated, all numbers, values and/or expressions referring to quantities of ingredients, reaction conditions, % absorption, and the like, that are used herein are to be understood as modified in all instances by the term "about."

Further, any numerical ranges disclosed herein will be understood to be continuous, and inclusive of every value between the minimum and maximum values of each range. Unless expressly indicated otherwise, such numerical ranges are approximations that are reflective of the various uncertainties of measurement encountered in obtaining such values.

The expected behavior of a pervaporation membrane made of a hydrophobic polymer is to become plasticized and/or swollen as the organic concentration increases. Plasticized and/or swollen membranes generally cause an undesirable increase in permeability of both the organic and water, with the water permeability generally increasing relatively more than the organic permeability thus resulting in a reduction in separation factor. Unexpectedly, polynorbornene pervaporation membranes, which are generally hydrophobic, exhibit a behavior opposite as to what is generally expected. Polynorbornene pervaporation membranes as described herein have a separation factor that increases dramatically with increasing feed concentration (that is, an increase in the organic concentration of a feed stream).

Typically in pervaporation, a multi-component liquid stream is passed across a pervaporation membrane that preferentially permeates one or more of the components. As the multi-component liquid stream flows across the pervaporation membrane surface, the preferentially permeated components pass through the pervaporation membrane and are removed as a permeate vapor. Transport through the pervaporation membrane is induced by maintaining a vapor pressure on the permeate side of the pervaporation membrane that is lower than the vapor pressure of the multi-component liquid stream. The vapor pressure difference can be achieved, for example, by maintaining the multi-component liquid stream at a higher temperature than that of the permeate stream. In this example, the latent heat of evaporation of the permeate components is supplied to the multi-component liquid stream for maintaining the feed temperature and for continuing the pervaporation process. Alternatively, the vapor pressure difference is typically achieved by operating at below atmospheric pressure on the permeate side of the pervaporation module. A partial vacuum on the permeate side of the polynorbornene pervaporation membrane can be obtained by any one of: relying on the pressure drop that occurs as a result of the cooling and condensation that takes place in the condenser unit, and/or by use of a vacuum pump. An optional sweep gas on the permeate side can facilitate the pervaporation process by lowering the concentration of the permeating components. The vapor pressure of the feed liquid can be optionally raised by heating the fermentation broth. While polynorbornene pervaporation membranes have already been disclosed in U.S. Pat. No. 8,215,496, pertinent disclosures of which are hereby incorporated by reference, and where such membranes have met with some success, the polynorbornene pervaporation membrane disclosed and claimed herein provide significant improvements over such previously disclosed membranes, which is apparent from the following disclosure.

As used herein, the symbol "〜" denotes a position at which the bonding takes place with another repeat unit or another atom or molecule or group or moiety as appropriate with the structure of the group as shown.

As used herein, the terms "polymer composition" or "homopolymer composition" or "copolymer composition" or "terpolymer composition" are used herein interchangeably and are meant to include at least one synthesized polymer or copolymer or terpolymer, as well as residues from initiators, catalysts and other elements attendant to the synthesis of such polymer, where such residues are generally understood as not being covalently incorporated thereto. However, in certain instances a catalyst employed during the polymerization step may still be covalently bound to the polymer. Such residues and other elements considered as part of the polymer composition are typically mixed or co-mingled with the polymer such that they tend to remain with the polymer when it is transferred between vessels or between solvent or dispersion media. A polymer composition can also include materials added after synthesis of the polymer to provide or modify specific properties to such composition. As used herein "homopolymer," "copolymer" or "terpolymer" refer to a polymer containing respectively one, two or three distinctive types of monomer repeat units. It is possible that the polymers disclosed herein may contain more than three distinctive types of monomeric repeat units and such polymers shall be defined according to the number of distinctive monomeric repeat units, i.e., "quadpolymer," "pentapolymer," and the like.

As used herein, "hydrocarbyl" refers to a moiety or a group that contains only carbon and hydrogen, non-limiting examples being alkyl, cycloalkyl, aryl, aralkyl, alkaryl, and alkenyl. The term "halohydrocarbyl" refers to a hydrocarbyl group where at least one hydrogen has been replaced by a halogen. The term perhalocarbyl refers to a hydrocarbyl group where all of the hydrogens have been replaced by a halogen.

As used herein, "alkyl" refers to a linear (straight chained) or branched acyclic, saturated hydrocarbon group having a carbon chain length of, for example, from $C_1$ to $C_{25}$. Non-limiting examples of suitable linear, i.e., straight chained alkyl groups include, but are not limited to, methyl, ethyl, n-propyl, n-butyl, n-pentyl, n-hexyl, n-heptyl, n-octyl, n-decyl, and so on. Non-limiting examples of suitable branched alkyl groups include, but are not limited to, iso-propyl, iso-butyl, sec-butyl, tert-butyl, iso-pentyl, neo-pentyl, tert-pentyl, and so on. The derived term "alkylol" or "hydroxyalkyl" refers to alkyl groups that include one or more hydroxyl groups.

As used herein, the expression "$(C_1-C_6)$perfluoroalkyl" means that all of the hydrogen atoms in said alkyl group are replaced with fluorine atoms. Illustrative examples include trifluoromethyl and pentafluoroethyl, and straight-chained or branched heptafluoropropyl, nonafluorobutyl, undecafluoropentyl and tridecafluorohexyl groups. Derived expression, "$(C_1-C_6)$perfluoroalkoxy", is to be construed accordingly.

As used herein, the expression "cycloalkyl" includes all of the known cyclic radicals. Representative examples of "$(C_3-C_{12})$cycloalkyl" includes without any limitation cyclopropyl, cyclobutyl, cyclopentyl, cyclohexyl, cycloheptyl, cyclooctyl, and the like. Derived expressions such as "cycloalkoxy", "cycloalkylalkyl", "cycloalkylaryl", "cycloalkylcarbonyl" are to be construed accordingly.

As used herein, the expression "bicycloalkyl" includes all of the known bicyclic radicals. Representative examples of "$(C_6-C_{12})$bicycloalkyl" includes without any limitation bicyclo[2.1.1]hexane, bicyclo[2.2.1]heptane, bicyclo[[3.2.1]octane, bicyclo[2.2.2]octane, bicyclo[3.2.2]nonane, bicyclo[3.3.1]nonane, bicyclo[3.3.2]decane, bicyclo[4.3.1]decane, bicyclo[4.4.1]undecane, bicyclo[5.4.1]dodecane, and the like. Derived expressions such as "bicycloalkoxy", "bicycloalkylalkyl", "bicycloalkylaryl", "bicycloalkylcarbonyl" are to be construed accordingly.

As used herein, the expression "tricycloalkyl" includes all of the known tricyclic radicals. Representative examples of "$(C_7-C_{14})$tricycloalkyl" includes without any limitation tricyclo[2.2.1.0$^{2,6}$]heptane, tricyclo[3.2.1.0$^{2,4}$]octane, tricyclo[4.2.1.0$^{2,5}$]nonane, octahydro-1H-4,7-methanoindene, octahydro-1H-4,7-ethano indene, octahydro-1H-cyclopropa[a]pentalene, decahydrocyclopenta[cd]pentalene, dodecahydro-1H-phenalene, adamantyl and the like. Derived expressions such as "tricycloalkoxy", "tricycloalkylalkyl", "tricycloalkylaryl", "tricycloalkylcarbonyl" are to be construed accordingly.

As used herein the term "aryl" refers to aromatic groups that include, without limitation, groups such as phenyl, biphenyl, benzyl, xylyl, naphthalenyl, anthracenyl, phenanthranyl, and the like. Generally "aryl" groups as referred to herein are monovalent or divalent moieties. Other "aryl" groups as contemplated herein include but not limited to any of the monovalent or divalent moieties derived from triphenylamine, diphenylamine, triphenylmethane, diphenylmethane, and the like. Similarly, "substituted aryl," such as "substituted phenyl" or "substituted naphthyl" shall include any of the possible substituents as further defined herein or one known in the art. Derived expressions, such as "arylsulfonyl," are to be construed accordingly.

As used herein, the expression "arylalkyl" or "aralkyl" or "alkaryl" means that the $(C_6-C_{10})$aryl as defined herein is further attached to $(C_1-C_{25})$alkyl as defined herein. Representative examples include benzyl, phenylethyl, 2-phenylpropyl, 1-naphthylmethyl, 2-naphthylmethyl and the like. Similarly, another derived expression "arylcycloalkyl" shall be construed accordingly. Representative examples of said expression include without any limitation, phenylcyclopropyl, 1-naphthylcyclopropyl, phenylcyclohexyl, 2-naphthylcyclopentyl, and the like. The aryl group can be further substituted, if desired. Non-limiting examples of suitable substituent groups for the aryl group include, among others, hydroxyl groups, benzyl groups, carboxylic acid and carboxylic acid ester groups and aliphatic hydrocarbon groups. The alkyl group can be substituted with halogens.

As used herein, the expression "heteroaryl" includes all of the known heteroatom containing aromatic groups. Representative 5-membered heteroaryl groups include furanyl, thienyl or thiophenyl, pyrrolyl, isopyrrolyl, pyrazolyl, imidazolyl, oxazolyl, thiazolyl, isothiazolyl, and the like. Representative 6-membered heteroaryl groups include pyridinyl, pyridazinyl, pyrimidinyl, pyrazinyl, triazinyl, and the like. Representative examples of bicyclic heteroaryl groups include, benzofuranyl, benzothiophenyl, indolyl, quinolinyl, isoquinolinyl, cinnolyl, benzimidazolyl, indazolyl, pyridofuranyl, pyridothienyl, and the like.

"Halogen" or "halo" means chloro, fluoro, bromo, and iodo.

In a broad sense, the term "substituted" is contemplated to include all permissible substituents of organic compounds. In a few of the specific embodiments as disclosed herein, the term "substituted" means substituted with one or more substituents independently selected from the group consisting of $(C_1-C_6)$alkyl, $(C_2-C_6)$alkenyl, $(C_1-C_6)$perfluoroalkyl, phenyl, hydroxy, —$CO_2H$, an ester, an amide, $(C_1-C_6)$alkoxy, $(C_1-C_6)$thioalkyl, $(C_1-C_6)$perfluoroalkoxy, —$NH_2$, Cl, Br, I, F, —NH-lower alkyl, and —N(lower alkyl)$_2$. However, any of the other suitable substituents known to one skilled in the art can also be used in these embodiments.

As used herein the term "thermolysis" means dissociation of compounds by heat and not to be construed as decomposition.

Monomers

Embodiments in accordance with the present invention are suitable for the preparation of polymers encompassing a wide range of "polycyclic" repeating units. As defined herein, the terms "polycyclic olefin" or "polycycloolefin" mean the same and are used interchangeably to represent the compounds of this invention. As a representative example of such a compound or a monomer is "norbornene-type" monomer and is generally referred to herein as addition polymerizable monomer (or the resulting repeating unit) or ring-opening metathesis polymerizable monomer (ROMP), that encompass at least one norbornene moiety such as shown below:

The simplest norbornene-type or polycyclic olefin monomer encompassed by embodiments in accordance with the present invention is the bicyclic monomer, bicyclo[2.2.1]hept-2-ene, commonly referred to as norbornene. However, the term norbornene-type monomer or repeating unit is used herein to mean norbornene itself as well as any substituted norbornene(s), or substituted and unsubstituted higher cyclic derivatives thereof. Representative examples of such monomers include but not limited to bicyclo[2.2.2]oct-2-ene, 7-oxabicyclo[2.2.1]hept-2-ene, 7-thiabicyclo[2.2.1]hept-2-ene, 7-azabicyclo[2.2.1]hept-2-ene, 1,2,3,4,4a,5,8,8a-octahydro-1,4:5,8-dimethanonaphthalene, 1,4,4a,5,6,7,8,8a-octahydro-1,4-epoxy-5,8-methanonaphthalene, and the like.

Thus in accordance with embodiments of this invention there is provided a compound of formula (I):

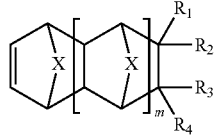

(I)

wherein:

each occurrence of X independently represents —$CH_2$—, —$CH_2$—$CH_2$—, O, S, and —NH—;

m is an integer from 0 to 5 inclusive;

at least one of $R_1$, $R_2$, $R_3$ and $R_4$ independently represents -L-($C_7$-$C_{14}$)tricycloalkyl or a group of formula (A):

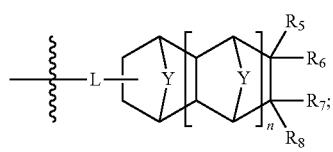

(A)

wherein:

each occurrence of Y independently represents —$CH_2$—, —$CH_2$—$CH_2$—, O, S, and —NH—;

n is an integer from 0 to 5 inclusive; and $R_5$, $R_6$, $R_7$ and $R_8$ independently represents hydrogen, methyl, ethyl, linear or branched ($C_3$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, ($C_5$-$C_{10}$)heteroaryl, ($C_5$-$C_{10}$)heteroaryl($C_1$-$C_3$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy, ($C_1$-$C_6$)acyloxy and halogen;

L represents a bond, $(CH_2)_o$, $((CH_2)_pO)_q$, $((CH_2)_pO(CH_2)_q)$, —$C_6H_4CH_2OCH_2C_6H_4$—, —$C_6H_4OCH_2C_6H_4$—, —$C_6H_4CH_2OC_6H_4$— or —$C_6H_4OC_6H_4$ where o, p and q independently are integers from 0 to 3 inclusive; or $R_1$ and $R_3$ taken together with the carbon atom to which they are attached form a substituted or unsubstituted ($C_5$-$C_7$) cycloalkyl or ($C_6$-$C_{12}$)bicycloalkyl ring;

remaining one or more of $R_1$, $R_2$, $R_3$ and $R_4$ independently represents hydrogen, methyl, ethyl, linear or branched ($C_3$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$) alkyl, ($C_5$-$C_{10}$)heteroaryl, ($C_5$-$C_{10}$)heteroaryl($C_1$-$C_3$) alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy, ($C_1$-$C_6$)acyloxy and halogen;

wherein each of aforementioned groups, where valence is permissible, is optionally substituted with one or more groups selected from ($C_1$-$C_6$)alkyl, ($C_3$-$C_7$)cycloalkyl, ($C_1$-$C_6$)perfluoroalkyl, halogen, hydroxy, acetoxy, phenyl, hydroxyphenyl, acetoxyphenyl and a group of formula (B):

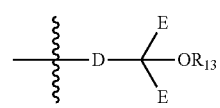

(B)

wherein:

D is $(CH_2)_r$ where r is an integer from 0 to 5 inclusive, phenylene, $C_6H_4(CH_2)_s$ where s is an integer from 1 to 3 inclusive, or $((CH_2)_t$—$O)_u$ where t and u independently are integers from 1 to 4 inclusive;

E is methyl, ethyl, $CF_3$ or $C_2F_5$; and $R_{13}$ is hydrogen or ($C_1$-$C_5$)alkyl.

As noted above any of the groups defined within the definitions of $R_1$, $R_2$, $R_3$ or $R_4$ can additionally be substituted optionally with one or more of aforementioned groups. In one of the embodiments, one of $R_1$, $R_2$, $R_3$ or $R_4$ is -L-($C_7$-$C_{14}$)tricycloalkyl, where L is a bond, $CH_2$, $CH_2O$ or O, and the ($C_7$-$C_{14}$)tricycloalkyl is optionally substituted one or more times with ($C_1$-$C_6$)alkyl, ($C_3$-$C_7$)cycloalkyl, ($C_1$-$C_6$) perfluoroalkyl, halogen, hydroxy, acetoxy, phenyl, hydroxyphenyl, acetoxyphenyl, $C(CF_3)_2OH$, $CH_2C(CF_3)_2OH$, $(CH_2)_2C(CF_3)_2OH$ or $(CH_2)_3C(CF_3)_2OH$.

In some embodiments in accordance with the present invention, the compound represented by formula (I) is defined by the following substituents: X is $CH_2$, m is 0; each of $R_2$, $R_3$ and $R_4$ is hydrogen, $R_1$ being a group of formula (A), wherein Y is $CH_2$, n is 1, L is a bond, and is represented by formula (II):

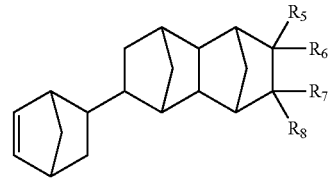

(II)

wherein:

each occurrence of $R_5$, $R_6$, $R_7$ and $R_8$ independently represents hydrogen, methyl, ethyl, n-propyl, iso-propyl, n-butyl, iso-butyl, sec-butyl, tert-butyl, $CF_3$, phenyl, benzyl, hydroxy, acetoxy, methoxy, ethoxy, n-propoxy, iso-propoxy, n-butoxy, iso-butoxy, tert-butoxy, $C_6H_4OH$, $C_6H_4OAc$, $C(CF_3)_2OH$, $CH_2C(CF_3)_2OH$, $(CH_2)_2C(CF_3)_2OH$, $(CH_2)_3C(CF_3)_2OH$ and $C_6H_4C(CF_3)_2OH$.

In some other embodiments of this invention, the compound represented by formula (I) is defined by the following substituents: X is $CH_2$, m is 0; each of $R_2$, $R_3$ and $R_4$ is hydrogen, $R_1$ being a group of formula (A), wherein Y is $CH_2$, n is 0, L is a bond, and is represented by formula (III):

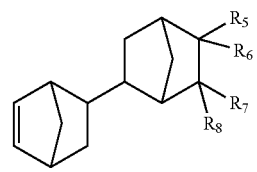

(III)

wherein:

each occurrence of $R_5$, $R_6$, $R_7$ and $R_8$ independently represents hydrogen, methyl, ethyl, n-propyl, iso-propyl, n-butyl, iso-butyl, sec-butyl, tert-butyl, $CF_3$, phenyl, benzyl, hydroxy, acetoxy, methoxy, ethoxy, n-propoxy, iso-propoxy, n-butoxy, iso-butoxy, tert-butoxy, $C_6H_4OH$, $C_6H_4OAc$, $C(CF_3)_2OH$, $CH_2C(CF_3)_2OH$, $(CH_2)_2C(CF_3)_2OH$, $(CH_2)_3C(CF_3)_2OH$ and $C_6H_4C(CF_3)_2OH$.

A few of the representative compounds encompassed by compound of formula (I) of this invention without any limitation are listed below:

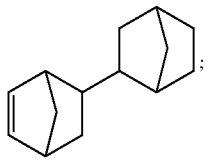

2-(bicyclo[2.2.1]hept-5-en-2-yl)bicyclo[2.2.1]heptane (also referred to herein as NBNBA)

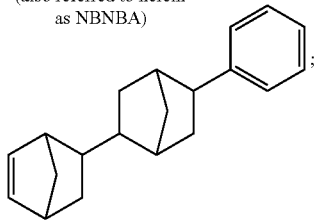

2-(bicyclo[2.2.1]hept-5-en-2-yl)-5-phenyl-bicyclo[2.2.1]heptane (also referred to herein as NBNBAPh)

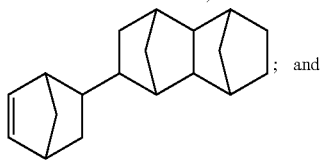; and 2-(bicyclo[2.2.1]hept-5-en-2-yl)decahydro-1,4:5,8-dimethanonaphthalene (also referred to herein as NBDDMN)

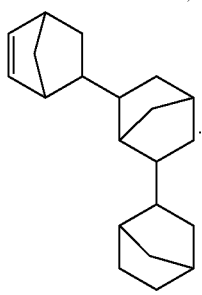

2-bicyclo[2.2.1]heptenyl)-6-bicyclo[2.2.1]heptylbicyclo[2.2.1]heptane
(NB-NBA-NBA)

In yet other embodiments of this invention, the compound represented by formula (I) is defined by the following substituents: m is 0; $R_1$ is ($C_7$-$C_{14}$)tricycloalkyl, which is optionally substituted with a group selected from ($C_1$-$C_6$) alkyl, ($C_3$-$C_7$)cycloalkyl, ($C_1$-$C_6$)perfluoroalkyl, halogen, hydroxy, acetoxy, phenyl, hydroxyphenyl, acetoxyphenyl, $C(CF_3)_2OH$, $CH_2C(CF_3)_2OH$, $(CH_2)_2C(CF_3)_2OH$, $(CH_2)_3C(CF_3)_2OH$ and $C_6H_4C(CF_3)_2OH$.

In still other embodiments, the compound represented by formula (I) is defined by the following substituents: X is $CH_2$, m is 0 and is represented by the formula (IV):

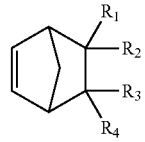

(IV)

wherein:

$R_1$ is 1-adamantyl or 2-adamantyl, which is optionally substituted one or more times with methyl, ethyl, n-propyl, iso-propyl, n-butyl, iso-butyl, sec-butyl, tert-butyl, $CF_3$, phenyl, benzyl, halogen, hydroxy, acetoxy, methoxy, ethoxy, n-propoxy, iso-propoxy, n-butoxy, iso-butoxy, tert-butoxy, $C_6H_4OH$, $C_6H_4OAc$, $C(CF_3)_2OH$, $CH_2C(CF_3)_2OH$, $(CH_2)_2C(CF_3)_2OH$, $(CH_2)_3C(CF_3)_2OH$ and $C_6H_4C(CF_3)_2OH$; and each occurrence of $R_2$, $R_3$, and $R_4$ independently represents hydrogen, methyl, ethyl, n-propyl, iso-propyl, n-butyl, iso-butyl, sec-butyl, tert-butyl, $CF_3$, phenyl, benzyl, hydroxy, acetoxy, methoxy, ethoxy, n-propoxy, iso-propoxy, n-butoxy, iso-butoxy, tert-butoxy, $C_6H_4OH$, $C_6H_4OAc$, $C(CF_3)_2OH$, $CH_2C(CF_3)_2OH$, $(CH_2)_2C(CF_3)_2OH$, $(CH_2)_3C(CF_3)_2OH$ and $C_6H_4C(CF_3)_2OH$.

A representative compound of embodiments that encompasses the compound of formula IV, without any limitation can be enumerated as:

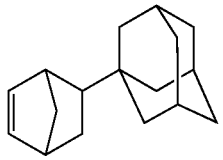

1-(bicyclo[2.2.1]hept-5-en-2-yl)adamantane (also referred to herein as NB-Ad).

In yet other embodiments, representative compounds encompassed by compound of formula (I), including compounds of formulae (II) to (IV) are enumerated, without any limitation, as follows:

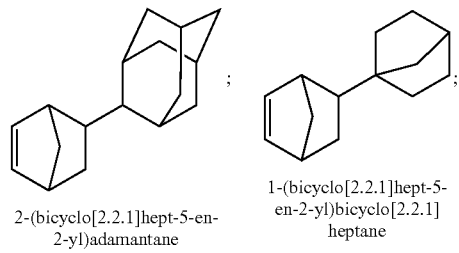

2-(bicyclo[2.2.1]hept-5-en-2-yl)adamantane 1-(bicyclo[2.2.1]hept-5-en-2-yl)bicyclo[2.2.1]heptane -continued

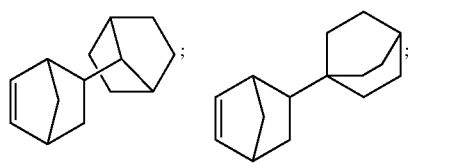

7-(bicyclo[2.2.1]hept-5-en-2-yl)bicyclo[2.2.1]heptane 1-(bicyclo[2.2.1]hept-5-en-2-yl)bicyclo[2.2.2]octane

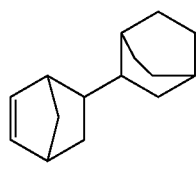

2-(bicyclo[2.2.1]hept-5-en-2-yl)bicyclo[2.2.2]octane

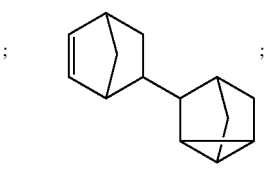

3-(bicyclo[2.2.1]hept-5-en-2-yl)tricyclo[2.2.1.0²,⁶]heptane

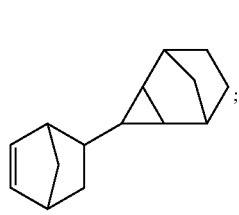

3-(bicyclo[2.2.1]hept-5-en-2-yl)tricyclo[3.2.1.0²,⁴]octane

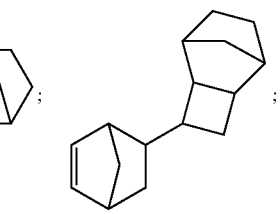

3-(bicyclo[2.2.1]hept-5-en-2-yl)tricyclo[4.2.1.0²,⁵]nonane

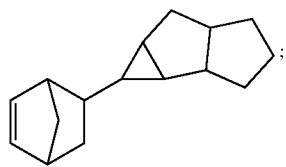

1-(bicyclo[2.2.1]hept-5-en-2-yl)octahydro-1H-cyclopropa[a]pentalene

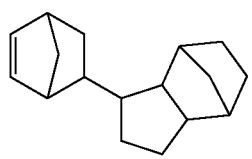

1-(bicyclo[2.2.1]hept-5-en-2-yl)octahydro-1H-4,7-methanoindene 1-(bicyclo[2.2.1]hept-5-en-2-yl)octahydro-1H-4,7-ethanoindene

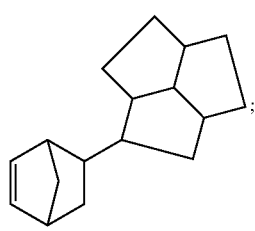

1-(bicyclo[2.2.1]hept-5-en-2-yl)decahydrocyclopenta[cd]pentalene

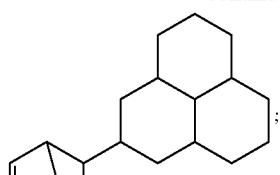

2-(bicyclo[2.2.1]hept-5-en-2-yl)dodecahydro-1H-phenalene

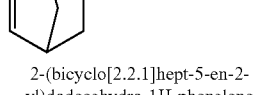

5′,5′,6′-trimethyl-2-(bicyclo[2.2.1]hept-5-en-2-yl)bicyclo[2.2.1]heptane

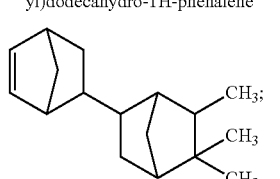

7′,7′-dimethyl-2-(bicyclo[2.2.1]hept-5-en-2-yl)bicyclo[2.2.1]heptane 2,3,4,4a,4b,5,8,8a,9,9a-decahydro-1H-1,4;5,8-dimethanofluorene

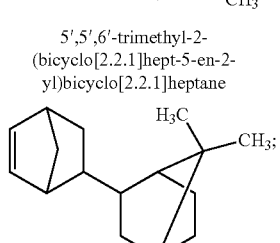

1-(bicyclo[2.2.1]hept-5-en-2-ylmethoxy)adamantane

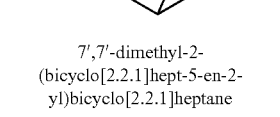

1-(bicyclo[2.2.1]hept-5-en-2-ylmeth)adamantane

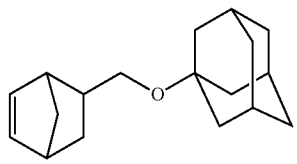

1-(bicyclo[2.2.1]hept-5-en-2-yloxy)adamantane 5-(bicyclo[2.2.1]heptan-2-ylmethyl)bicyclo[2.2.1]hept-2-ene

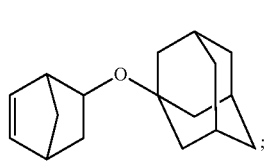

5-(bicyclo[2.2.1]heptan-2-yloxy)bicyclo[2.2.1]hept-2-ene

; and

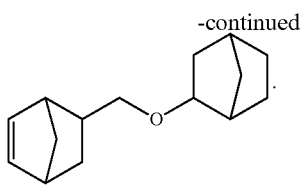

5-((bicyclo[2.2.1]heptan-2-yloxy)methyl)bicyclo[2.2.1]hept-2-ene

It has been observed that various other monomeric compounds can also be used in the preparation of polymers of this invention which are not encompassed by the compounds of formula (I). Representative examples of such monomers without any limitations may be enumerated as follows:

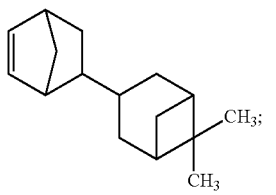

3-(bicyclo[2.2.1]hept-5-en-2-yl)6,6-dimethylbicyclo[3.1.1]heptane

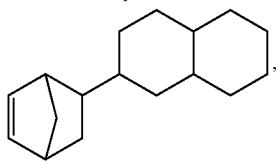

2-(bicyclo[2.2.1]hept-5-en-2-yl)decahydronaphthalene

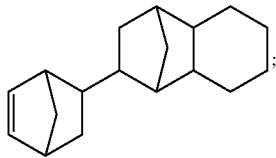

2-(bicyclo[2.2.1]hept-5-en-2-yl)decahydro-1,4-methanonaphthalene

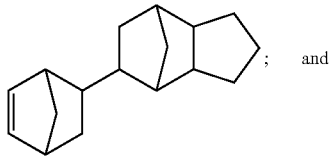

; and 5-(bicyclo[2.2.1]hept-5-en-2-yl)octahydro-1H-4,7 methanoindene

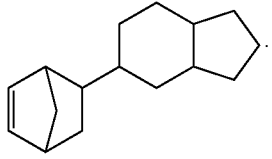

5-(bicyclo[2.2.1]hept-5-en-2-yl)octahydro-1H-indene

The compounds of this invention can be synthesized by any of the procedures known to one skilled in the art. Specifically, several of the starting materials used in the preparation of the compounds of this invention are known or are themselves commercially available. The compounds of this invention and several of the precursor compounds may also be prepared by methods used to prepare similar compounds as reported in the literature and as further described herein. See for instance, U.S. Pat. No. 6,825,307.

In general, an economical route for the preparation of compounds of formula (I), wherein m=0, (also compounds of formula (II) to (IV)) relies on the Diels-Alder addition reaction in which a compound of formula (VI), e.g., cyclopentadiene or its analogs, such as 1,3-cyclohexadiene, furan, thiophene or pyrrole (i.e., X=$CH_2$, —$CH_2$—$CH_2$—, O, S, or NH) is reacted with a suitable dienophile of formula (VII) at suitable reaction temperatures which are typically at elevated temperatures to form the compounds of formula (I) generally shown by the following reaction scheme I:

Scheme I

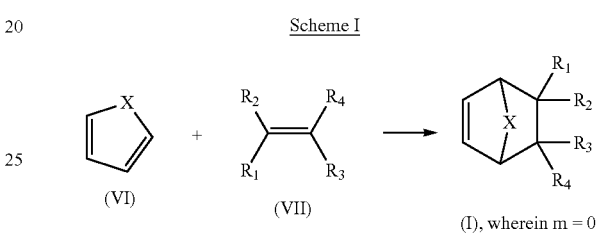

wherein $R_1$, $R_2$, $R_3$ and $R_4$ are as defined herein.

Other compounds of formula (I), wherein m=1 to 5, can also be prepared similarly, for example when X=$CH_2$, by the thermolysis of dicyclopentadiene (DCPD, VIII) in the presence of a suitable dienophile of formula (VII). The reaction proceeds by the initial thermolysis of DCPD (VIII) to cyclopentadiene (CPD) (i.e., compound of formula (VI), where X=$CH_2$) followed by the Diels-Alder addition of CPD and the dienophile of formula (VII) and subsequent additions with a dienophile of formula (I), wherein X=$CH_2$ and m=0, and so on, to give the adducts shown below in Scheme II:

Scheme II

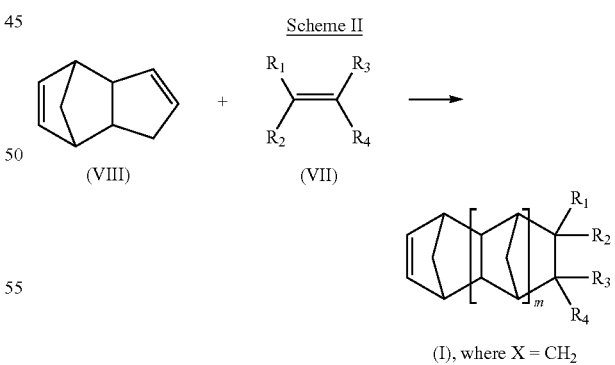

wherein m, $R_1$, $R_2$, $R_3$ and $R_4$ are as defined herein.

The dienophile of formula (VII) is either generally available commercially or can be prepared following any of the known literature procedures. In general, the dienophile of formula (VII) is either a L-($C_7$-$C_{14}$)tricycloalkyl compound substituted with a desired olefinic group, i.e., a compound of formula (VIIA) or an olefinic compound of formula (VIIB):

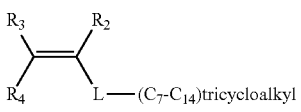

(VIIA)

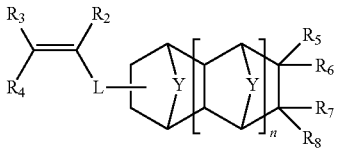

(VIIB)

Polymers

Embodiments in accordance with the present invention also provide a polymer comprising a first type of repeating unit represented by formula (IA), said repeating unit is derived from a monomer of formula (I):

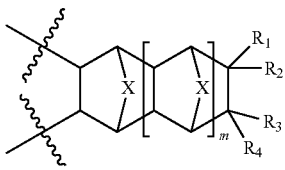

(IA)

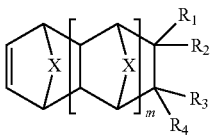

(I)

wherein:
each occurrence of X independently represents —CH$_2$—, —CH$_2$—CH$_2$—, O, S, and —NH—;
m is an integer from 0 to 5 inclusive;
at least one of R$_1$, R$_2$, R$_3$ and R$_4$ independently represents -L-(C$_7$-C$_{14}$)tricycloalkyl or a group of formula (A):

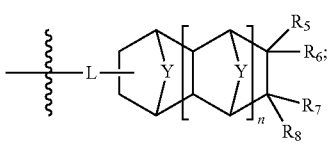

(A)

wherein:
each occurrence of Y independently represents —CH$_2$—, —CH$_2$—CH$_2$—, O, S, and —NH—;
n is an integer from 0 to 5 inclusive; and
R$_5$, R$_6$, R$_7$ and R$_8$ independently represents hydrogen, methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, (C$_5$-C$_{10}$)heteroaryl, (C$_5$-C$_{10}$)heteroaryl(C$_1$-C$_3$)alkyl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy(C$_1$-C$_3$)alkyl, (C$_5$-C$_{10}$)heteroaryloxy(C$_1$-C$_3$)alkyl, (C$_6$-C$_{10}$)aryloxy, (C$_5$-C$_{10}$)heteroaryloxy, (C$_1$-C$_6$)acyloxy and halogen;

L represents a bond, (CH$_2$)$_o$ or ((CH$_2$)$_p$O)$_q$, ((CH$_2$)$_p$O(CH$_2$)$_q$), —C$_6$H$_4$CH$_2$OCH$_2$C$_6$H$_4$—, —C$_6$H$_4$OCH$_2$C$_6$H$_4$—, —C$_6$H$_4$CH$_2$OC$_6$H$_4$— or —C$_6$H$_4$OC$_6$H$_4$—, where o, p and q independently are integers from 0 to 3 inclusive; or
R$_1$ and R$_3$ taken together with the carbon atom to which they are attached form a substituted or unsubstituted (C$_5$-C$_7$)cycloalkyl or (C$_6$-C$_{12}$)bicycloalkyl ring;
remaining one or more of R$_1$, R$_2$, R$_3$ and R$_4$ independently represents hydrogen, methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, (C$_5$-C$_{10}$)heteroaryl, (C$_5$-C$_{10}$)heteroaryl(C$_1$-C$_3$)alkyl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy(C$_1$-C$_3$)alkyl, (C$_5$-C$_{10}$)heteroaryloxy(C$_1$-C$_3$)alkyl, (C$_6$-C$_{10}$)aryloxy, (C$_5$-C$_{10}$)heteroaryloxy, (C$_1$-C$_6$)acyloxy and halogen;
wherein each of aforementioned groups, where valence is permissible, is optionally substituted with a group selected from (C$_1$-C$_6$)alkyl, (C$_3$-C$_7$)cycloalkyl, (C$_1$-C$_6$)perfluoroalkyl, halogen, hydroxy, acetoxy, phenyl, hydroxyphenyl, acetoxyphenyl and a group of formula (B):

(B)

wherein:
D is (CH$_2$)$_r$ where r is an integer from 1 to 5 inclusive, phenylene, C$_6$H$_4$(CH$_2$)$_s$ where s is an integer from 1 to 3 inclusive, or ((CH$_2$)$_t$—O)$_u$ where t and u independently are integers from 1 to 4 inclusive;
E is methyl, ethyl, CF$_3$ or C$_2$F$_5$; and
R$_{13}$ is hydrogen or (C$_1$-C$_5$)alkyl.

As noted above any of the groups defined within the definitions of R$_1$, R$_2$, R$_3$ or R$_4$ can additionally be substituted optionally with one or more of aforementioned groups. In one of the embodiments, one of R$_1$, R$_2$, R$_3$ or R$_4$ is -L-(C$_7$-C$_{14}$)tricycloalkyl, where L is a bond, CH$_2$, CH$_2$O or O, and the (C$_7$-C$_{14}$)tricycloalkyl is optionally substituted one or more times with (C$_1$-C$_6$)alkyl, (C$_3$-C$_7$)cycloalkyl, (C$_1$-C$_6$)perfluoroalkyl, halogen, hydroxy, acetoxy, phenyl, hydroxyphenyl, acetoxyphenyl, C(CF$_3$)$_2$OH, CH$_2$C(CF$_3$)$_2$OH, (CH$_2$)$_2$C(CF$_3$)$_2$OH or (CH$_2$)$_2$C(CF$_3$)$_2$OH.

Such first type of repeating unit, represented by formula (IA), of such polymer composition can be defined by the following substituents: R$_1$ being a group of formula (A), R$_5$ is phenyl, X and Y are CH$_2$, m is 0, n is 0 or 1 and L is a bond. Further, in this embodiment each of R$_2$, R$_3$, R$_4$, R$_6$, R$_7$ and R$_8$ is hydrogen. Alternatively, such first type of repeating unit can be defined by the following substituents: R$_1$ being a group of formula (A), X and Y are CH$_2$, m is 0, n is 0 or 1 and L is a bond. Further, in this embodiment each of R$_2$, R$_3$, R$_4$, R$_5$, R$_6$, R$_7$ and R$_8$ is hydrogen. Still further, such first type of repeating unit can be defined by X is CH$_2$, R$_1$ is 1-adamantyl and m is 0. Further, in this embodiment each of R$_2$, R$_3$ and R$_4$ is hydrogen.

In other polymer embodiments of the present invention the polymer as described herein further comprises a second repeating unit represented by formula (VA), said second repeat unit is derived from the monomer of formula (V):

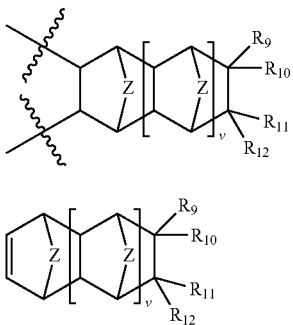

(VA)

(V)

wherein:
each occurrence of Z independently represents —CH$_2$—, —CH$_2$—CH$_2$—, O, S, and —NH—;
v is an integer from 0 to 5 inclusive;
R$_9$, R$_{10}$, R$_{11}$ and R$_{12}$ independently represents hydrogen, methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_5$-C$_{10}$)heteroaryl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy, (C$_5$-C$_{10}$)heteroaryloxy, (C$_1$-C$_6$)acyloxy and halogen or a group of formula (B):

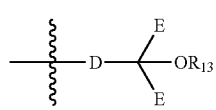

(B)

wherein:
D is (CH$_2$)$_r$ where r is an integer from 1 to 5 inclusive, phenylene, C$_6$H$_4$(CH$_2$)$_s$ where s is an integer from 1 to 3 inclusive, or ((CH$_2$)$_t$—O)$_u$ where t and u independently are integers from 1 to 4 inclusive;
E is methyl, ethyl, CF$_3$ or C$_2$F$_5$; and
R$_{13}$ is hydrogen or (C$_1$-C$_5$)alkyl; and
wherein each of aforementioned groups, where valence is permissible, is optionally substituted with a group selected from (C$_1$-C$_6$)alkyl, (C$_3$-C$_7$)cycloalkyl, (C$_6$-C$_{12}$)bicycloalkyl, (C$_7$-C$_{14}$)tricycloalkyl, (C$_6$-C$_{10}$)aryl, (C$_1$-C$_6$)perfluoroalkyl, halogen, hydroxy, acetoxy, phenyl, hydroxyphenyl, acetoxyphenyl and a group of formula (B):

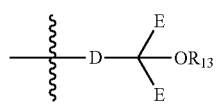

(B)

wherein D, E and R$_{13}$ are as defined hereinabove.

In another embodiment of the polymer, Z is —CH$_2$—, v is 0, each of R$_{10}$, R$_{11}$ and R$_{12}$ is hydrogen and R$_9$ is —CH$_2$C(CF$_3$)$_2$OH. This polymer embodiment is further defined by R$_1$ being a group of formula (A), X and Y are —CH$_2$—, m and n are 0, R$_5$ is phenyl, each of R$_2$, R$_3$, R$_4$, R$_6$, R$_7$ and R$_8$ is hydrogen.

In yet another embodiment the polymer is defined by R$_1$ being a group of formula (A), X and Y are —CH$_2$—, m is 0, n is 0 or 1, each of R$_2$, R$_3$, R$_4$, R$_5$, R$_6$, R$_7$ and R$_8$ is hydrogen.

In yet another embodiment the polymer is defined by X is —CH$_2$—, m is 0, each of R$_2$, R$_3$ and R$_4$ is hydrogen and R$_1$ is adamantyl.

In another embodiment the polymer composition consists of a first type of polycyclic repeating units of formula (IIA):

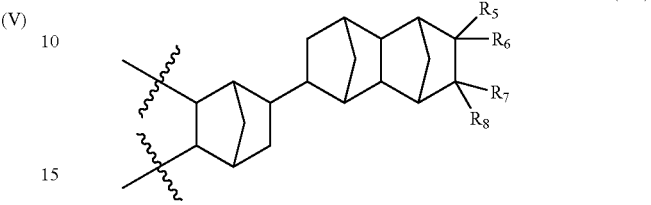

(IIA)

wherein R$_5$, R$_6$, R$_7$ and R$_8$ are as defined herein.

In another embodiment the polymer composition consists of a first type of polycyclic repeating units of formula (IIIA):

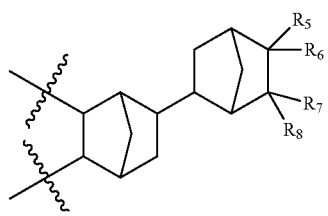

(IIIA)

wherein R$_5$, R$_6$, R$_7$ and R$_8$ are as defined herein.

In another embodiment the polymer composition consists of a first type of polycyclic repeating units of formula (IVA):

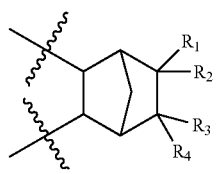

(IVA)

wherein R$_1$, R$_2$, R$_3$ and R$_4$ are as defined herein.

It will be noted that generally polymers in accordance with the present invention encompass one or more types of first repeat units derived from monomer types represented by formula (I), particularly formulae (II), (III) or (IV), and at least one other type of repeat unit derived from a monomer of formula (V) as described herein.

Accordingly, the polymer of this invention generally contains both of the first repeating units derived from monomer types represented by formula (I), and the second repeat units derived from a monomer of formula (V) as disclosed herein in various molar ratio. Thus, in an embodiment of this invention the molar ratio of the first repeat unit and the second repeat unit is generally from about 1:99 to about 99:1. In another embodiment the molar ratio of first repeating unit to second repeating unit is from about 20:80 to about 80:20. In yet another embodiment the molar ratio of first repeating unit to second repeating unit is from about 40:60 to about 60:40. In another embodiment the molar ratio of first repeating unit to second repeating unit is from about 45:55 to about 55:45. In some other embodiments the molar ratio of first repeating unit to second repeating unit is 50:50.

In one of the embodiments of the present invention the polymer as described herein is a copolymer derived from at least one first repeating unit derived from the monomer of formula (I) listed below without any limitation:

2-(bicyclo[2.2.1]hept-5-en-2-yl)bicyclo[2.2.1]heptane;
2-(bicyclo[2.2.1]hept-5-en-2-yl)-5-phenyl-bicyclo[2.2.1]heptane;
2-(bicyclo[2.2.1]hept-5-en-2-yl)decahydro-1,4:5,8-dimethanonaphthalene;
2-(bicyclo[2.2.1]heptenyl)-6-bicyclo[2.2.1]heptylbicyclo[2.2.1]heptane;
1-(bicyclo[2.2.1]hept-5-en-2-yl)adamantane;
2-(bicyclo[2.2.1]hept-5-en-2-yl)adamantane;
1-(bicyclo[2.2.1]hept-5-en-2-yl)bicyclo[2.2.1]heptane;
2-(bicyclo[2.2.1]hept-5-en-2-yl)bicyclo[2.2.1]heptane;
1-(bicyclo[2.2.1]hept-5-en-2-yl)bicyclo[2.2.2]octane;
2-(bicyclo[2.2.1]hept-5-en-2-yl)bicyclo[2.2.2]octane;
3-(bicyclo[2.2.1]hept-5-en-2-yl)tricyclo[2.2.1.0²,⁶]heptane;
3-(bicyclo[2.2.1]hept-5-en-2-yl)tricyclo[3.2.1.0²,⁴]octane;
3-(bicyclo[2.2.1]hept-5-en-2-yl)tricyclo[4.2.1.0²,⁵]nonane;
1-(bicyclo[2.2.1]hept-5-en-2-yl)octahydro-1H-cyclopropa[a]pentalene;
1-(bicyclo[2.2.1]hept-5-en-2-yl)octahydro-1H-4,7-methanoindene;
1-(bicyclo[2.2.1]hept-5-en-2-yl)octahydro-1H-4,7-ethanoindene;
1-(bicyclo[2.2.1]hept-5-en-2-yl)decahydrocyclopenta[cd]pentalene;
2-(bicyclo[2.2.1]hept-5-en-2-yl)dodecahydro-1H-phenalene;
5',5',6'-trimethyl-2-(bicyclo[2.2.1]hept-5-en-2-yl)bicyclo[2.2.1]heptane;
7',7'-dimethyl-2-(bicyclo[2.2.1]hept-5-en-2-yl)bicyclo[2.2.1]heptane;
2,3,4,4a,4b,5,8,8a,9,9a-decahydro-1H-1,4:5,8-dimethanofluorene;
1-(bicyclo[2.2.1]hept-5-en-2-ylmethoxy)adamantane;
1-(bicyclo[2.2.1]hept-5-en-2-ylmethyl)adamantane;
1-(bicyclo[2.2.1]hept-5-en-2-yloxy)adamantane;
5-(bicyclo[2.2.1]heptan-2-ylmethyl)bicyclo[2.2.1]hept-2-ene;
5-(bicyclo[2.2.1]heptan-2-yloxy)bicyclo[2.2.1]hept-2-ene;
5-((bicyclo[2.2.1]heptan-2-yloxy)methyl)bicyclo[2.2.1]hept-2-ene;
3-(bicyclo[2.2.1]hept-5-en-2-yl)-6,6-dimethylbicyclo[3.1.1]heptane;
2-(bicyclo[2.2.1]hept-5-en-2-yl)decahydronaphthalene;
2-(bicyclo[2.2.1]hept-5-en-2-yl)decahydro-1,4-methanonaphthalene;
5-(bicyclo[2.2.1]hept-5-en-2-yl)octahydro-1H-4,7-methanoindene; and
5-(bicyclo[2.2.1]hept-5-en-2-yl)octahydro-1H-indene.

In yet another embodiment of this invention there is provided a copolymer encompassed by a first repeating unit of the formula (IVA) where $R_1$ is a group of formula A where L is a bond, n is 0 or 1, Y is $CH_2$, $R_2$, $R_3$, $R_4$, $R_5$, $R_6$, $R_7$ and $R_8$ are each independently hydrogen, methyl, ethyl or phenyl, and a second repeating unit of formula (VA) where Z is $CH_2$, v is 0, at least one of $R_9$, $R_{10}$, $R_{11}$ and $R_{12}$ is methyl, ethyl, linear or branched $(C_3-C_6)$alkyl or $(C_3-C_8)$cycloalkyl or a group of formula B, and the remaining $R_5$, $R_6$, $R_7$ and $R_8$ are hydrogen.

In particular, the second type of repeating unit can be derived from any one of the following monomers without any limitation:

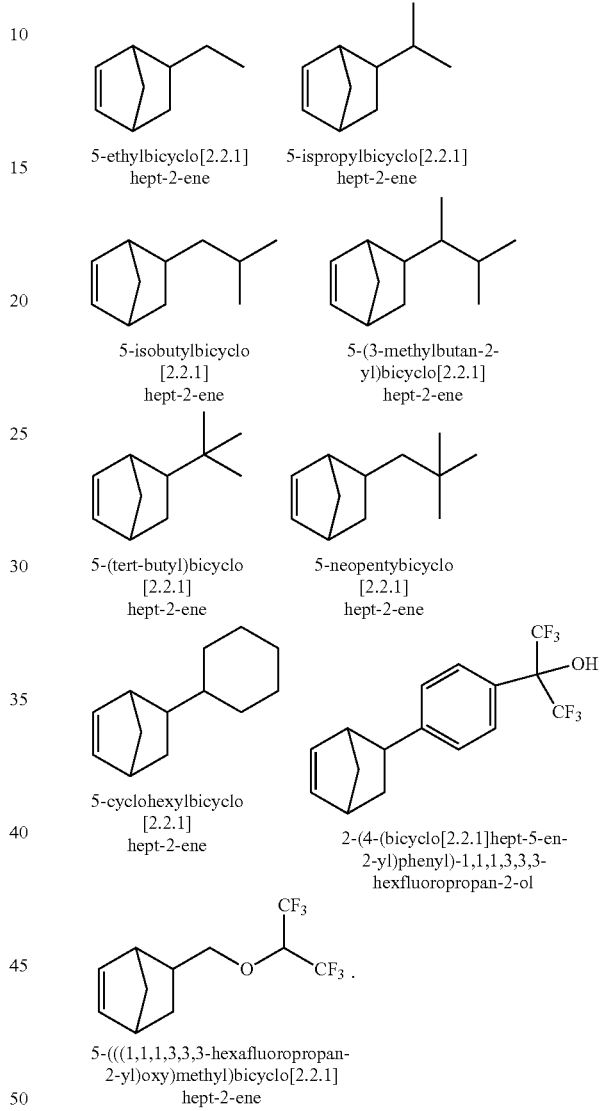

In yet other embodiments in accordance with the present invention representative examples of the following copolymers without any limitation are enumerated:

a copolymer of 2-(bicyclo[2.2.1]hept-5-en-2-yl)bicyclo[2.2.1]heptane and hydroxyhexafluoroisopropylmethylnorbornene (NBNBA/HFANB);

a copolymer of 2-(bicyclo[2.2.1]hept-5-en-2-yl)bicyclo[2.2.1]heptane and norbornene (NBNBA/NB);

a copolymer of 2-(bicyclo[2.2.1]hept-5-en-2-yl)-5-phenyl-bicyclo[2.2.1]heptane and hydroxyhexafluoroisopropylmethylnorbornene (NBNBAPh/HFANB);

a copolymer of 2-(bicyclo[2.2.1]hept-5-en-2-yl)decahydro-1,4:5,8-dimethanonaphthalene and hydroxyhexafluoroisopropylmethylnorbornene (NBDDMN/HFANB);

a copolymer of 1-(bicyclo[2.2.1]hept-5-en-2-yl)adamantane and hydroxyhexafluoroisopropylmethylnorbornene (NB-Ad/HFANB);

a copolymer of 2-(bicyclo[2.2.1]hept-5-en-2-yl)adamantane and hydroxyhexafluoroisopropylmethylnorbornene (NB-2Ad/HFANB);

a copolymer of 2-(bicyclo[2.2.1]hept-5-en-2-yl)bicyclo[2.2.1]heptane and 5-(((1,1,1,3,3,3-hexafluoropropan-2-yl)oxy)methyl)bicyclo[2.2.1]hept-2-ene (NBNBA/NBCH$_2$OCH(CF$_3$)$_2$); and a copolymer of 2-(bicyclo[2.2.1]hept-5-en-2-yl)bicyclo[2.2.1]heptane and 5-n-butylbicyclo[2.2.1]hept-2-ene (NBNBA/BuNB);

a copolymer of 2-(bicyclo[2.2.1]hept-5-en-2-yl)bicyclo[2.2.1]heptane and 5-n-hexylbicyclo[2.2.1]hept-2-ene (NBNBA/HexylNB);

a copolymer of 2-(bicyclo[2.2.1]hept-5-en-2-yl)decahydro-1,4:5,8-dimethanonaphthalene and 5-n-decylbicyclo[2.2.1]hept-2-ene (NBDDMN/DecylNB); and a copolymer of 2-(bicyclo[2.2.1]hept-5-en-2-yl)bicyclo[2.2.1]heptane and 2-(4-(bicyclo[2.2.1]hept-5-en-2-yl)phenyl)-1,1,1,3,3,3-hexafluoropropan-2-ol (NBNBA/NBPh(CF$_3$)$_2$OH).

In another embodiment of this invention the polymer of this invention is a terpolymer, i.e., it encompasses any three monomer repeat units as described herein, i.e., any three of the repeat units derived from monomers of formulae (I) to (V). For example, the first and second repeating units may be derived from monomers of formulae (I) to (IV), and the third repeat unit is derived from a monomer of formula (V). In the alternative, the first repeating unit is derived from any one of the monomers of formulae (I) to (IV), and the second and third repeat units are derived from two distinctive monomers of formula (V). Representative examples of such terpolymers include without any limitation NBNBA/BuNBA/HFANB, NBNBA/HexylNB/HFANB, NBDDMN/DecylNB/HFANB, and the like. Various other monomers and combinations thereof as described can be employed to such terpolymers of this invention. Further any molar ratios of the three monomers to form the terpolymer can be employed. For instance, such molar ratios can range from 98:1:1 to 1:98:1 to 1:1:98, i.e., any theoretically possible combination of ratios can be employed. In some of the embodiments the ratios range from 5:5:90 to 5:90:5 to 90:5:5; from 10:10:80 to 10:80:10 to 80:10:10, and so on.

In another embodiment of this invention the polymers of this invention include four or more monomers selected from any of the monomers represented by formulae (I) to (V).

In one of the embodiments of this invention the polymer of this invention is a copolymer of 2-(bicyclo[2.2.1]hept-5-en-2-yl)bicyclo[2.2.1]heptane and hydroxyhexa-fluoroisopropyl-methylnorbornene (NBNBA/HFANB).

In another embodiment of this invention the polymer of this invention is a copolymer of 2-(bicyclo[2.2.1]hept-5-en-2-yl)bicyclo[2.2.1]heptane and 5-n-butylbicyclo[2.2.1]hept-2-ene (NBNBA/BuNB).

In another embodiment of this invention the polymer of this invention is a copolymer of 2-(bicyclo[2.2.1]hept-5-en-2-yl)bicyclo[2.2.1]heptane and norbornene (NBNBA/NB).

Polymer Preparation

In general, one or more monomers of formula (I), particularly monomers of formulae (II) to (IV), as described herein can be polymerized along with one or more monomers of formula (V) to form the polymers of this invention containing the respective monomeric repeat units as represented by formula (IA) or (VA). Any of the polymerization methods can be employed to form the polymer compositions of this invention. For instance, polymerization of various norbornene-type monomers is disclosed in U.S. Pat. Nos. 5,929,181; 6,455,650; 6,825,307; and 7,101,654. In general, the polymerization can be carried out either in solution using a desirable solvent or in mass, and in both instances, suitably in the presence of a catalyst. Any of the known catalyst system which brings about the polymerization of the compounds of formula (I) or compounds of formula (V) can be used. The catalyst is generally added to the reaction medium containing the desired monomer(s), i.e., the compounds of formula (I) or (V) as a preformed single component catalyst or the catalyst can be formed in situ.

For example, in a solution process, the polymerization reaction is carried out by adding a solution of the preformed catalyst or individual catalyst components to a solution of the compound of formula (I), i.e., the monomer(s) to be polymerized. In some embodiments, the amount of monomer dissolved in the solvent ranges from about 5 to about 50 weight percent (wt. %), and in other embodiments from about 10 to about 30 wt. %, and in still other embodiments from about 10 to about 20 wt. %. After the preformed catalyst or catalyst components are added to the monomer solution, the reaction medium is agitated (e.g., stirred) to ensure complete mixing of catalyst and monomer components.

The polymerization can further be carried out at suitable temperature, such as at ambient temperature or at superambient temperatures for a period of time adequate for the polymerization. In certain situations, depending upon the type of monomer involved and depending upon the type of catalysts employed subambient reaction temperatures can also be used. More specifically, the polymerization reaction temperatures can range from about 0° C. to about 150° C. In some embodiments the reaction temperature can range from about 10° C. to about 100° C., and in some other embodiments the reaction temperature can range from about 20° C. to about 80° C.

In some embodiments, the compounds of formula (I), including monomers of formula (II), (III) or (IV) of this invention, along with monomers of formula (V), can be polymerized under a free radical polymerization conditions. Such free radical polymerization procedures are particularly useful when using any of the electron poor olefins as described further below. Typically in a free radical polymerization process, the monomers are polymerized in a solvent at an elevated temperature (about 50° C. to about 150° C.) in the presence of a free radical initiator. Suitable initiators include but are not limited to azo compounds and peroxides. Examples of free radical initiators are azobisisobutyronitrile (AIBN), benzoyl peroxide, lauryl peroxide, azobisisocapronitrile, azobisisovaleronitrile, tert-butylhydroperoxide and di-tert-butylperoxide.

In one of the embodiments of this invention the free radical catalyst initiators are particularly useful when polymerizing the compounds of formula (I) in combination with an one or more electron poor olefins selected from acrylic acid, methacrylic acid, maleic acid, itaconic acid, citraconic anhydride, itaconic anhydride, maleic anhydride, and linear or branched (C$_1$ to C$_5$) alkyl esters of acrylic acid, sulfur dioxide, or a mixture of two or more thereof.

Nickel containing catalysts useful for making the polymers utilized in this invention may be represented by the formula:

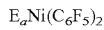

$$E_aNi(C_6F_5)_2$$

wherein a is 1 or 2 and E represents a neutral 2 electron donor ligand. When a is 1, E is generally a pi-arene ligand such as toluene, benzene, and mesitylene. When a is 2, E is selected from diethyl ether, tetrahydrofuran (THF), ethyl acetate (EtOAc) and dioxane. The ratio of monomer to catalyst in the reaction medium can range from about 5000:1 to about 50:1 in some embodiments of the invention, and in other embodiments at a ratio of about 2000:1 to about 100:1. The reaction may be run in a suitable solvent at a temperature range from about 0° C. to about 70° C. In some embodiments, the temperature can range from about 10° C. to about 50° C., and in other embodiments from about 20° C. to about 40° C. Exemplary catalysts of the above formula include (toluene)bis(perfluorophenyl)nickel, (mesitylene)bis(perfluorophenyl)nickel, (benzene)bis(perfluorophenyl) nickel, bis(tetrahydrofuran)bis(perfluorophenyl)nickel, bis (ethyl acetate)bis(perfluorophenyl)nickel and bis(dioxane) bis(perfluorophenyl)nickel.

Palladium containing catalysts useful for making the polymers utilized in this invention can be prepared as a preformed single component catalyst or prepared in situ by admixing a palladium containing procatalyst with an activator in the presence of the desired monomer(s) to be polymerized.

The preformed catalyst can be prepared by admixing the catalyst precursors such as a procatalyst and activator in an appropriate solvent, allowing the reaction to proceed under appropriate temperature conditions, and isolating the reaction product, a preformed catalyst product. By procatalyst is meant a palladium containing compound that is converted to an active catalyst by a reaction with a cocatalyst or activator compound. Further description and synthesis of representative procatalysts and activator compounds can be found in U.S. Pat. No. 6,455,650, as noted above.

Palladium procatalysts suitable for the polymerization of the compounds of this invention are represented by the formula:

(Allyl)Pd(P(R$_3$)$_3$)(L$_1$)

wherein R is selected from isopropyl and cyclohexyl; and L$_1$ is selected from trifluoroacetate, and trifluoromethanesulfonate (triflate). Representative procatalyst compounds in accordance with such formula are (allyl)palladium(tricyclohexylphosphine)triflate, (allyl)palladium(tri-isopropylphosphine)triflate, (allyl)palladium(tri-cyclohexylphosphine)trifluoroacetate, and (allyl)palladium(tri-isopropylphosphine)trifluoroacetate.

Representative activator compounds may be selected from lithium tetrakis(pentafluorophenyl)borate etherate (Li-FABA=[Li(OEt$_2$)$_{2.5}$][B(C$_6$F$_5$)$_4$]) and N,N-dimethylanilinium tetrakis(pentafluorophenyl)borate (DANFABA).

In one of the embodiments of this invention, a palladium compound, Pd(OC(O)CH$_3$)$_2$, a phosphine compound, and the activators, LiFABA or DANFABA, referred to above can be mixed in situ with the desired monomer(s) to be polymerized. Representative phosphine compounds are phosphines such as tricyclohexylphosphine and triisopropylphosphine.

In another embodiment of the invention, the molar ratio of palladium procatalyst (based on the palladium metal) to activator is 1 to 2. In another embodiment, the ratio is 1 to 4, and in another embodiment the ratio is 1 to 1. It should be noted that the order of addition of the various catalyst components mentioned above to the reaction medium is not important.

The palladium catalysts in accordance with the present invention may exhibit a high activity at monomer to procatalyst molar ratios (i.e., monomer to palladium metal) of over 100,000:1. In some embodiments of the invention, monomer to procatalyst ratios can range from about 100:1 to about 1,000,000:1. In other embodiments, from about 1,000:1 to about 500,000:1, and in still other embodiments from about 2,500:1 to about 250,000:1. Depending on the activity of a particular catalyst, the reactivity of a certain monomer, the desired molecular weight, or desired polymer backbone tacticity, higher concentrations of catalyst to monomer loading are well within the scope of the present invention (i.e., monomer to catalyst loadings of 50:1 to 99,999:1).

Various other palladium catalysts have also been reported in the literature which can be used in the vinyl addition polymerization method of this invention to form polymers of this invention starting from various monomers of formula (I) in combination with a monomer of formula (V). See for example, U. S. Patent Publication No. 20050187398 A1, which discloses certain of the palladium catalysts that can be used in the solution or mass polymerization of various polycyclic olefinic monomers. The palladium catalysts as disclosed therein are of the formula (C) or (D) as represented below:

[(E(R)$_3$)$_b$Pd(Q)(LB)$_c$]$_d$[WCA]$_e$  (C)

[(E(R)$_3$)(E(R)$_2$R*)Pd(LB)]$_d$[WCA]$_e$  (D)

In Formula (C), E(R)$_3$ represents a Group 15 neutral electron donor ligand where E is selected from a Group 15 element of the Periodic Table of the Elements, and R independently represents hydrogen (or one of its isotopes), or an anionic hydrocarbyl containing moiety; Q is an anionic ligand selected from a carboxylate, thiocarboxylate, and dithiocarboxylate group; LB is a Lewis base; WCA represents a weakly coordinating anion; b represents an integer of 1, 2, or, 3; c represents an integer of 0, 1, or 2, where the sum of b+c is 1, 2, or 3; and d and e are integers that represent the number of times the palladium cation and the weakly coordinating anion are taken to balance the electronic charge on the structure of formula (C).

In Formula (D), E(R$_3$) is as defined for Formula (C), and E(R)$_2$R* also represents a Group 15 neutral electron donor ligand where E, R, d and e are defined as above and where R* is an anionic hydrocarbyl containing moiety, bonded to the Pd and having a β hydrogen with respect to the Pd center.

Exemplary palladium catalysts within the scope of formula (C) or (D) include but not limited to the following:
[Pd(OAc)(P(Cy)$_3$)$_2$(MeCN)][B(C$_6$F$_5$)$_4$],
[Pd(OAc)(P(Cy)$_2$(CMe$_3$))$_2$(MeCN)][B(C$_6$F$_5$)$_4$],
[Pd(OAc)(P(i-Pr)(CMe$_3$)$_2$)$_2$(MeCN)][B(C$_6$F$_5$)$_4$],
[Pd(OAc)$_2$(P(i-Pr)$_2$(CMe$_3$))$_2$(MeCN)][B(C$_6$F$_5$)$_4$],
[Pd(OAc)(P(i-Pr)$_3$)$_2$(MeCN)][B(C$_6$F$_5$)$_4$],
[Pd(O$_2$C-t-Bu)(P(Cy)$_3$)$_2$(MeCN)][B(C$_6$F$_5$)$_4$]
[Pd(O$_2$C-t-Bu)(P(Cy)$_2$(CMe$_3$))$_2$(MeCN)][B(C$_6$F$_5$)$_4$],
[Pd(O$_2$C-t-Bu)$_2$(P(i-Pr)$_2$(CMe$_3$))$_2$,
[Pd(O$_2$C-t-Bu)(P(i-Pr)$_3$)$_2$(MeCN)][B(C$_6$F$_5$)$_4$],
cis-[Pd(P(i-Pr)$_3$)(κ$^2$-P,C—P(i-Pr)$_2$(C(CH$_3$)$_2$)(MeCN)][B(C$_6$F$_5$)$_4$], and
cis-[Pd(P(i-Pr)$_3$)(κ$^2$-P,C—P(i-Pr)$_2$(C(CH$_3$)$_2$)(NC$_5$H$_5$)][B(C$_6$F$_5$)$_4$.
wherein OAc is acetate, Cy is cyclohexyl, MeCN is acetonitrile, Me is methyl, i-Pr is isopropyl, t-Bu is tert-butyl, and κ$^2$ is bidentate.

Suitable polymerization solvents for the free radical and vinyl addition polymerization reactions include hydrocarbon, haloalkane and aromatic solvents. Exemplary hydrocarbon solvents include but are not limited to alkanes and cycloalkanes such as pentane, hexane, heptane and cyclohexane. Exemplary haloalkane solvents include but or not limited to dichloromethane, chloroform, carbon tetrachloride, ethylchloride, 1,1-dichloroethane, 1,2-dichloroethane, 1-chloropropane, 2-chloropropane, 1-chlorobutane, 2-chlorobutane, 1-chloro-2-methylpropane, 1-chloropentane, Freon™ 112 halocarbon solvent. Exemplary aromatic solvents include but are not limited to benzene, toluene, xylene, mesitylene, chlorobenzene, and o-dichlorobenzene. Other organic solvents such as diethyl ether, tetrahydrofuran, acetates (e.g., ethyl acetate) and other esters, lactones, ketones and amides are also useful. Mixtures of one or more of the foregoing solvents can be utilized as a polymerization solvent. In some embodiments the solvents employed include cyclohexane, toluene, mesitylene, dichloromethane, 1,2-dichloroethane, and water.

When utilizing the vinyl-addition nickel and palladium catalysts disclosed above, the molecular weight of the polymer can be controlled by employing a chain transfer agent disclosed in U.S. Pat. No. 6,136,499. In one embodiment of the invention, silanes, such as t-butyl silane, triethylsilane, and the like, α-olefins, (e.g., ethylene, propylene, 1-hexene, 1-decene, 4-methyl-1-pentene) and cyclohexene are suitable as molecular weight control agents.

In some of the embodiments, the polymers of this invention can be prepared by ring-opening metathesis polymerization (ROMP) by utilizing at least one monomer of formula (I) optionally with at least one monomer of formula (V) in the presence of a suitable catalyst. See, for example, carbazole-functionalized norbornene ROMP polymers have been found to have high separation factors for the dehydration of alcohols, Wang et al., "Pervaporation separation of aqueous alcohol solution through a carbazole-functionalized norbornene derivative membrane using living ring-opening metathesis polymerization", *Journal of Membrane Science*, 246 (2005) 59-65. The ROMP generally results in a polymer having the repeat units of formula (IB) as shown in Scheme III, wherein X, m, $R_1$, $R_2$, $R_3$, and $R_4$ are as defined herein, and x is a number of repeat units. The compound of formula (IB) can be used as such or can be hydrogenated to a polymer having the repeat units of the formula (IC). The monomer of formula (V) similarly undergoes ROMP to provide corresponding repeat units which can further be hydrogenated.

Scheme III

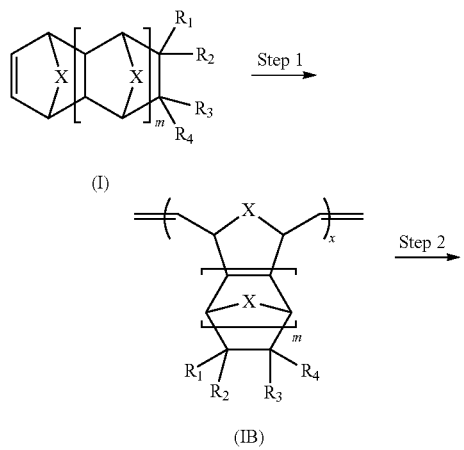

(I)

(IB)

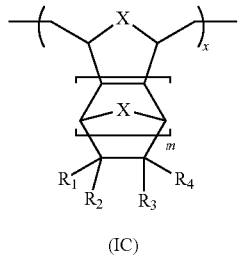

(IC)

In Scheme III, Step 1, the desired monomer, such as monomer of formula (I) is reacted with a suitable ROMP catalyst to form the polymer of formula (IB). Any of the known ROMP catalysts can be used in Step 1, Scheme III in order to carry out the polymerization step. For example, it has been reported that certain of the group VIII metals, such as ruthenium trichloride, $RuCl_3$, catalyzes the ring opening polymerization of the norbornene-type monomers of formula (I) in a suitable solvent including aqueous solutions. It has also been reported that such polymerization reactions can also be carried out by employing other than the group VIII metal catalysts, such as titanium, tantalum, molybdenum or tungsten metathesis catalysts or initiators. Other bicomponent catalysts such as tungsten hexachloride ($WCl_6$)/ethyl aluminum dichloride ($EtAlCl_2$), $WCl_6$/tetrabutyl tin ($BuSn_4$) and molybdenum trioxide ($MoO_3$)/silica ($SiO_2$) have also been found to be effective as ROMP catalysts. It is believed that the polymerization reaction is catalyzed through the formation of metal alkylidene (also known as metal-carbene) complexes. Exemplary ruthenium catalysts for ROMP polymerization include without any limitation the following:

$RuCl_3$/water mixture;
$RuCl_3$/ethanol mixture;
$(P(Ph)_3)_2(Cl)_2(Ru=CH-CH=C(Ph)_2)$;
$(P(C_6H_{11})_3)_2(Cl)_2(Ru=CHPh)$;
[1,3-bis-(2,4,6-trimethylphenyl)-2-imidazolidinylidene]-(P$(C_6H_{11})_3$)($Cl)_2$(Ru=CHPh);
[1,3-bis-(2,4,6-trimethylphenyl)-2-dihydroimidazolidinylidene]-(P($C_6H_{11})_3$)($Cl)_2$(Ru=CHPh);

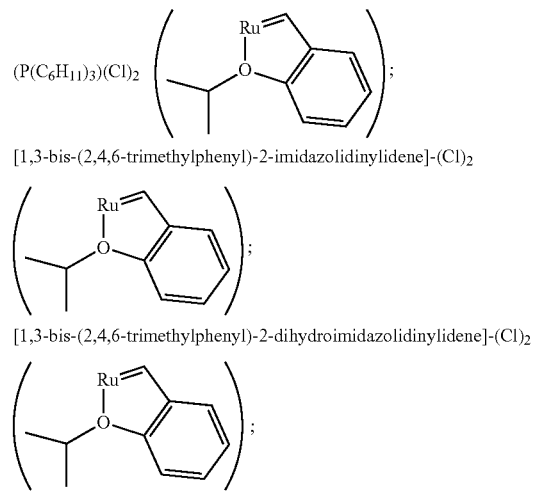

$(P(C_6H_{11})_3)(Cl)_2$

[1,3-bis-(2,4,6-trimethylphenyl)-2-imidazolidinylidene]-$(Cl)_2$

[1,3-bis-(2,4,6-trimethylphenyl)-2-dihydroimidazolidinylidene]-$(Cl)_2$ and
[1,3-bis-(2,4,6-trimethylphenyl)-2-dihydroimidazolidinylidene]-(3-bromopyridine)$_2$($Cl)_2$(Ru=CHPh).

Exemplary molybdenum catalysts for ROMP polymerization include without any limitation the following:

2,6-diisopropylphenylimidoneophylidene molybdenum(VI) bis(t-butoxide);

2,6-diisopropylphenylimidoneophylidene molybdenum(VI) bis(hexafluoro-t-butoxide) (also known as Schrock's catalyst);

2,6-diisopropylphenylimidoneophylidenemolybdenum(VI) bis(trifluoromethanesulfonate) dimethoxyethane adduct;

2,6-diisopropylphenylimidoneophylidene[racemic-BIPHEN]molybdenum(VI);

2,6-diisopropylphenylimidoneophylidene[(R)-(+)-BIPHEN]molybdenum(VI); and 2,6-diisopropylphenylimidoneophylidene[(S)-(−)-BIPHEN]molybdenum(VI);

The ROMP reactions to form the polymers comprising the repeat units of formula (IB) can be carried out in a variety of solvents depending upon the desired type of polymer formed therefrom. The ROMP can be carried out using one or more monomers of formula (I) and one or more monomers of formula (V) together under ROMP conditions. In some embodiments the polymerization is carried out using at least one monomer of formula (I) together with at least one monomer of formula (V). Generally, the monomers are metered into the reaction mixture containing the catalyst solution. In some other embodiments the catalyst solution is added to the reaction mixture containing one or more of distinct types of monomers in the solution. In some other embodiments a solution of at least one monomer of formula (I) and a solution of at least one monomer of formula (V) are added to the reaction mixture sequentially to a reaction mixture containing the catalyst solution. Exemplary solvents include without any limitation methanol, ethanol, butanol, dichloromethane, 1,2-dichloroethane, 1,1-dichloroethane, carbon tetrachloride, and mixtures thereof.

The polymerization can further be carried out at suitable temperature, such as at ambient temperature or at superambient temperatures for a period of time adequate for the polymerization. In certain situations, depending upon the type of monomer involved and depending upon the type of catalysts employed subambient reaction temperatures can also be used. In some embodiments, the polymerization is carried out at ambient reaction temperature, i.e., around 25° C. In some other embodiments, the polymerization reaction temperatures can range from about 0° C. to about 150° C. In some embodiments the reaction temperature can range from about 10° C. to about 100° C., and in some other embodiments the reaction temperature can range from about 20° C. to about 80° C.

In Scheme III, Step 2, the resulting polymer from the ROMP is hydrogenated using any of the methods known in the art. Typically, the ROMP polymer containing the repeat units of formula (IB) is dissolved in a suitable solvent and reacted with a suitable hydrogenation agent, such as for example any of the known hydrazide compounds. Examples of suitable hydrogenation agents include without any limitation p-toluenesulfonylhydrazide and 1,3,5-triisopropylbenzenesulfonylhydrazide. Various other known hydrogenation catalysts, e.g., Pd/C or Pd/CaCO$_3$ can also be used to hydrogenate ROMP polymers of this invention.

It has now been found that the polymers formed in accordance with the ROMP polymerization method disclosed herein provides polymers exhibiting high glass transition temperatures ($T_g$). The $T_g$s of these polymers can further be increased by providing bulky, rigid side groups, such as norbornane (i.e., NBNBA) or tetracyclododecane (i.e., NBDDMN).

It has been further observed that the hydrogenation of the ROMP polymer of formula (IB) to form the hydrogenated polymer of formula (IC) generally results in the lowering of $T_g$ of the resulting hydrogenated polymer of formula (IC), presumably, due to increasing segmental mobility of the backbone.

Accordingly, in some embodiments the ROMP polymer in accordance with this invention encompasses one or more of the following monomers without any limitation:

norbornene (NB);

2-(bicyclo[2.2.1]hept-5-en-2-yl)bicyclo[2.2.1]heptane (NBNBA);

2-(bicyclo[2.2.1]hept-5-en-2-yl)-5-phenyl-bicyclo[2.2.1]heptane (NBNBAPh);

2-(bicyclo[2 0.2.1]hept-5-en-2-yl)decahydro-1,4:5,8-dimethanonaphthalene (NBDDMN);

1-(bicyclo[2.2.1]hept-5-en-2-yl)adamantane (NB-Ad);

2-(bicyclo[2.2.1]hept-5-en-2-yl)adamantane (NB-2Ad);

5-n-butylbicyclo[2.2.1]hept-2-ene (BuNB);

5-n-hexylbicyclo[2.2.1]hept-2-ene (HexylNB);

5-n-decylbicyclo[2.2.1]hept-2-ene (DecylNB);

hydroxyhexafluoroisopropylmethylnorbornene (HFANB); and 5-(((1,1,1,3,3,3-hexafluoropropan-2-yl)oxy)methyl)bicyclo[2.2.1]hept-2-ene The polynorbornene polymers formed according to this invention generally exhibit a weight average molecular weight ($M_w$) of at least about 5,000. In another embodiment, the polynorbornene polymers used to make the polynorbornene pervaporation membranes has a $M_w$ of at least about 50,000. In yet another embodiment, the polynorbornene used to make the polynorbornene pervaporation membranes has a $M_w$ of at least about 150,000. In yet another embodiment, the polynorbornene used to make the polynorbornene pervaporation membranes has a $M_w$ of at least about 250,000. In yet another embodiment, the polynorbornene used to make the polynorbornene pervaporation membranes has a $M_w$ of at least about 400,000. In yet another embodiment, the polynorbornene used to make the polynorbornene pervaporation membranes has a $M_w$ of at least about 500,000. Generally, the larger the $M_w$, the more suitable the polynorbornene is for use in unsupported forms of the polynorbornene pervaporation membranes as further described herein. The $M_w$ of the polymers can be measured by any of the known methods such as by gel permeation chromatography (GPC) equipped with suitable detector and calibration standards, such as differential refractive index detector calibrated with narrow-distribution polystyrene standards. The polydispersity index (PDI=$M_w/M_n$) can then be measured, which is generally in the range of 1.1 to 3. The $M_n$ being the number average molecular weight.

Pervaporation Membranes

A suitable polymer of this invention comprising desirable repeat units of polycycloalkyl norbornene-type monomers of formula (I) and/or (V) is generally dissolved in a suitable organic solvent to form a solution. In one of the embodiments the polymer solution is of a copolymer of 2-(bicyclo[2.2.1]hept-5-en-2-yl)bicyclo[2.2.1]heptane and hydroxyhexafluoroisopropylmethylnorbornene (NBNBA/HFANB) or of a copolymer of 2-(bicyclo[2.2.1]hept-5-en-2-yl)bicyclo[2.2.1]heptane and norbornene (NBNBA/NB) or of a copolymer of 2-(bicyclo[2.2.1]hept-5-en-2-yl)bicyclo[2.2.1]heptane and 5-n-butylnorbornene (NBNBA/BuNB). The polymer solution is generally filtered through a suitable filter to remove any residual contaminants. After filtration, trapped gas can be removed. The polymer solution can then be formed into a film by any of the known methods in the art. For instance, the polymer solution is poured onto a substrate and pulled to form a film. The film is then dried and removed from the substrate, if any, and is ready for use. The films formed in this fashion are generally considered as single thickness films, specific examples of this embodiment are further described below. In some embodiments, the films are cast as double thickness films by forming a second layer of film on the first formed film. In some other embodiments the polymer solution is applied on to a polymer web to form a reinforced membrane, either on a sheet to form a supported membrane or on a substrate panel to form a non-supported membrane. In other embodiments the polymer solution can suitably cast to form a tubular composite, or a hollow fiber. Accordingly, in one of the embodiments, the pervaporation membrane of this invention is in a form of a tubular composite, hollow fiber, a dense film flat sheet, or a thin film composite.

The polynorbornene pervaporation membranes can be in any suitable form to effect separation of a desirable material, for example butanol, from a fermentation broth. Examples include spiral wound modules, fiber membranes including hollow fiber membranes, tubular membranes, and flat sheet membranes, such as in a plate and frame configuration, a supported or unsupported dense film, or a thin film composite.

When the polycycloalkyl polynorbornene pervaporation membranes are in an unsupported dense film form, the thickness of the dense film is from about 1 micron to about 500 microns. In another embodiment, the thickness of the dense film is from about 5 microns to about 100 microns.

When the polycycloalkyl polynorbornene pervaporation membranes are in the form of a thin film composite, such membranes can be thinner than unsupported membranes, for example as thin as about 0.1 microns. Further, the membrane contains at least one layer of polynorbornene and at least one layer of a non-polynorbornene component. Such composites can contain multiple layers of polynorbornene pervaporation membranes and multiple layers of non-polynorbornene component. Examples of the non-polynorbornene component include non-polynorbornene polymers and inorganic materials. Examples of non-polynorbornene polymers include polyethylenes including TYVEK®, polypropylenes, polyesters, polyimides, polycarbonates, polytetrafluoroethylene, poly(vinylidene fluoride) (PVDF), poly(methyl methacrylate) (PMMA), polyacrylonitrile (PAN), mixed co- and terpolymers thereof, and the like. Examples of inorganic materials include zeolites, glass frits, carbon powder, metal sieves, metal screens, metal frit, and the like.

A schematic diagram of the pervaporation process is shown in FIG. 1. As depicted, a feed containing numerous species is charged into a pervaporation module 100 and to a liquid chamber 102 on the feed side thereof. Vapor chamber 104 on the permeate side is separated from the liquid chamber 102 by a pervaporation membrane 106. The vapor phase is extracted from the feed liquid through the pervaporation membrane 106 which is selective for a given permeate, and the permeate vapor, which is enriched in the given permeate relative to the feed liquid, and is removed from the pervaporation module 100, generally by condensation thereof.

Utilizing polycycloalkyl polynorbornene pervaporation membranes, pervaporation can be employed to treat a fermentation broth containing, for example, biobutanol, ethanol or phenol and one or more other miscible components. More specifically, a fermentation broth can be added to the liquid chamber 102 and thus placed in contact with one side of polynorbornene pervaporation membrane 106 while a vacuum or gas purge is applied to vapor chamber 104. The fermentation broth can be heated or unheated. The components in the fermentation broth sorb into/onto polynorbornene pervaporation membrane 106, permeate through and evaporate into the vapor phase. The resulting vapor or permeate, for example butanol (or phenol), is then condensed and collected. Due to different species in the fermentation broth having different affinities for the polynorbornene pervaporation membrane and different diffusion rates through the membrane, even a component at low concentration in the feed can be highly enriched in the permeate. Accordingly, in one of the embodiments there is provided a pervaporation membrane, which is capable of preferential permeability to a volatile organic over water. The permeability of a volatile organic through pervaporation membrane of the present invention generally increases with increasing organic concentration of a feed stream.

Figure 2:
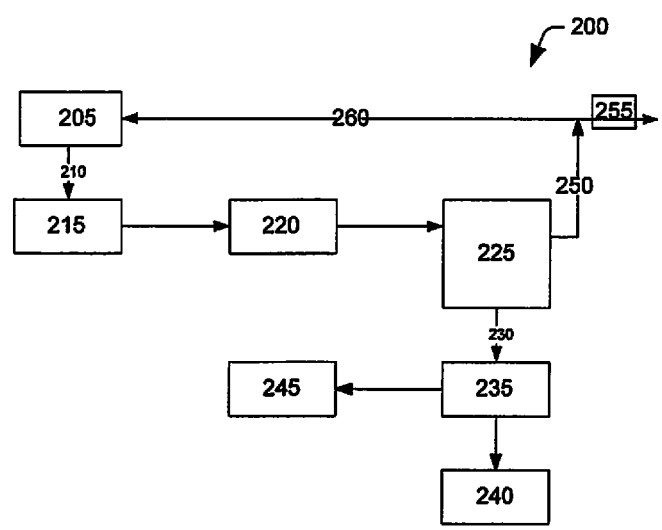
FIG. 2 depicts a pervaporation system in accordance with embodiments of the invention.

FIG. 2 depicts an exemplary pervaporation system 200 that can be employed to separate butanol, or other desirable materials, from a crude fermentation broth (or an aqueous industrial waste or other waste including biomass-waste) containing a valuable organic compound, such as biobutanol or phenol. Crude fermentation broth (or other waste including industrial and/or biomass) as a feed stream 210 from a feed tank 205 is pumped via pump 215 through a heater 220 to increase its temperature. The fermentation broth is then charged under pressure to a pervaporation module 225 containing a polynorbornene pervaporation membrane. Permeate vapor 230 containing butanol (or phenol) is obtained from the pervaporation module 225 by applying vacuum (using vacuum pump 245), where the butanol vapor (or phenol vapor) is condensed in a condenser 235, and collected in collector 240. Residual fermentation broth or retentate stream 250 that does not pass through the polynorbornene pervaporation membrane can be either discharged (255) from the system 200 or directed to a recycling stream 260 and returned to the feed tank 205.

Supplemental methods that complement the pervaporation process include removing solids from the fermentation broth by centrifugation, filtration, decantation, dephlegmation or the like; and increasing the concentration of butanol in the permeate using adsorption, distillation or liquid-liquid extraction or the like.

Butanol from biomass is often referred to as biobutanol. Biobutanol can be produced by fermentation of biomass by the acetone-butanol-ethanol fermentation (A.B.E.) process. See, for example, S-Y Li, et al. Biotechnol. Prog. 2011, vol. 27(1), 111-120. The process uses the bacterium of the genus *Clostridium*, such as *Clostridium acetobutylicum*, but others including *Saccharomyces cerevisiae, Zymomonas mobilis, Clostridium thermohydrosulfuricum, Escherichia coli, Candida pseudotropicalis*, and *Clostridium beijerinckii*, can be used. Biobutanol can also be made using genetically modified yeasts for the production of biobutanol from cellulosic materials. The crude fermentation broth containing biobutanol can be advantageously processed by the polynorbornene pervaporation membrane depicted in FIG. 1 and/or the pervaporation system depicted in FIG. 2 to provide concentrated butanol, as compared to the concentration thereof in the crude broth. Not withstanding the above, polynorbornene pervaporation membranes are useful for separation of various alcohols other than butanol, including ethanol and phenol from the respective fermentation broths or industrial or biomass waste.

Fermentation broths generally contain a variety of carbon substrates. In addition to the carbon source, fermentation broths can contain suitable minerals, salts, cofactors, buffers and other components, known to those skilled in the art, suitable for the growth of the cultures and promotion of the enzymatic pathway necessary for butanol production. Examples of fermentation broths that are commercially available include Luria Bertani (LB) broth, Sabouraud Dextrose (SD) broth, or Yeast Medium (YM) broth. Any of these known fermentation broths can be used in the present invention in order to separate the volatile organics from such broths.

Similarly, it should be noted that various other organic products are selectively formed from a fermentation process. For instance, phenol often termed as "green phenol" can be formed from appropriate waste, including biological waste or industrial waste, and by employing appropriate biological organisms to effect the fermentation to proceed selectively to phenol. It has been reported that phenol can be selectively produced from a recombinant strain of the solvent-tolerant bacterium *Pseudomonas putida* S12, see, for example, L. Heerema, et. al. Desalination, 200 (2006), pp 485-487. It has also been reported that various other yeast strains also produce phenol, all of which use bacterium of the genus *Saccharomyces*, such as *Saccharomyces cerevisiae* r.f. *bayanus*, EP 171 Lalvin; *Saccharomyces bayanus*, Ever; *Saccharomyces ellipsoideus*, Ceppo 20 *Castelli*; *Saccharomyces oviform's*, Ceppo 838 *Castelli*; *Saccharomyces cerevisiae* r.f. *cerevisiae*, K1 Lalvin; and *Saccharomyces cerevisiae*, D254 Lalvin. These organisms are able to produce different amounts of phenolic substance from a synthetic and/or natural organic sources whose main carbon source is glucose. See, M. Giaccio, J. Commodity Science (1999), 38(4), 189-200. In general, as used herein "green phenol" generically refers to phenol produced by a fermentation broth, which contains phenol from about 0.1% to about 6% phenol. In other embodiments, the fermentation broth contains from about 0.5% to about 3% phenol.

As used herein, "butanol" generically refers to n-butanol and its isomers. In some embodiments in accordance with the present invention, the fermentation broth contains from about 0.1% to about 10% butanol. In other embodiments, the fermentation broth contains from about 0.5% to about 6% butanol. In some other embodiments, the fermentation broth contains from about 1% to about 3% butanol. Generally, the polycycloalkyl polynorbornene pervaporation membranes described herein are effective at separating volatile organics, such as butanol, ethanol or phenol from fermentation broths containing relatively low to high levels of volatile organics, yet in some embodiments the fermentation broth contains at least about 1% volatile organics.

It should further be noted that certain of the "green phenol" feedstock can also be generated using phenolic based resins, such as novolak resins, and the like. Such feed streams can also be used in the pervaporation process of this invention where the phenol can be separated and/or enriched from the waste stream. Furthermore, various such phenol streams also contain certain inorganic and organic salts as impurities. As a result, it is difficult to remove such inorganic salts from the feed stream and to obtain phenol in the pure enriched form. However, surprisingly it has now been found that the pervaporation membranes of the instant invention are capable of separating such inorganic and organic salts. Representative examples of inorganic salts include, without any limitation, salts of lithium, sodium, potassium, magnesium, calcium, barium and the like. The salts of these metals with any counteranions can be used in this invention. Such examples of non-limiting anions include, phosphate, sulfate, acetate, benzoate, and the like. However, other anions such as methanesulfonate (mesylate), trifluoromethanesulfonate (triflate), p-toluenesulfonate (tosylate), and halides, such as fluoride, chloride, bromide and iodide can also be separated from the feed stream.

In one of the embodiments there is provided a process of separating an organic product from a feedstock selected from a fermentation broth or an industrial waste containing the organic product, such as butanol, ethanol, phenol, THF, ethyl acetate, acetone, toluene, MEK, MIBK, etc. In some embodiments, the fermentation broth is charged to a pervaporation module containing a pervaporation membrane formed by a polycyclic polynorbornene polymer as described herein. The permeate vapor containing the organic product from the pervaporation module is then collected. In this process, it may be advantageous to heat the crude fermentation broth feed to a temperature that facilitates the organic product passage through the polynorbornene pervaporation membrane of this invention. In one embodiment, the crude fermentation broth feed is heated to a temperature from about 30° C. to about 110° C. In another embodiment, the crude fermentation broth feed is heated to a temperature from about 40° C. to about 90° C. In yet another embodiment, the crude fermentation broth feed is heated to a temperature from about 50° C. to about 70° C. It should be noted that the desired temperature may depend upon the type of organics that is being separated. For example, relatively lower temperatures are employed in the separation of butanol whereas somewhat higher temperatures are desirable while separating phenol. Accordingly, in one of the embodiments the fermentation broth containing butanol feed is heated to a temperature in the range of from about 30° C. to about 90° C. In another embodiment the fermentation broth containing phenol feed is heated to a temperature in the range of from about 40° C. to about 110° C.

To facilitate pervaporation, a suitable vacuum can be applied to the vapor chamber of the pervaporation module. In one embodiment, the vacuum applied is from about 0.1 in Hg to about 25 in Hg. In another embodiment, the vacuum applied is from about 0.1 in Hg to about 4 in Hg. In another embodiment, the vacuum applied is from about 0.2 in Hg to about 4 in Hg.

Other processes include methods of increasing a separation factor for an organic product, such as butanol, phenol or ethanol, as a concentration of the organic product increases in a pervaporation feed stream. Such methods involve using a polynorbornene pervaporation membrane to separate the organic product from the pervaporation feed stream.

As used herein, "SF" is the separation factor which is a measure of quality of the separation of a first species relative to a second species and is defined as the ratio of the ratio of permeate compositions to the ratio of the feed compositions.

As used herein, flux is the amount that flows through a unit area of a membrane per unit of time.

Flux and SF can also be described by the following equations:

$$\text{Flux}(J) = \text{mass}/(\text{area} \cdot \text{time})$$

Separation Factor (SF)

$$SF_{12} = \left(\frac{y_1/y_2}{x_1/x_2}\right) = \left(\frac{J_1/J_2}{x_1/x_2}\right) = SF_{VLE} SF_{membrane}$$

$y$ = Permeate concentration, $x$ = Feed liquid concentration

Accordingly, the efficiency of a pervaporation membrane can be readily evaluated in two respects, a separation factor (the ratio of enrichment obtained when the liquid mixture permeates through the membrane) and the flux at which a liquid mixture permeates through the polymeric membrane. Thus, the higher the separation factor and flux of a membrane, the higher the separation efficiency of such membrane. Of course this is a very simplified analysis as low separation factors can often be overcome through the use of multistage membrane processes and where the flux factor of a membrane is low, often forming such a membrane with a high surface area can overcome low flux. Thus while the separation and flux factors are important considerations, other factors such as a membrane's strength, elasticity, resistance to becoming fouled during use, thermal stability, free volume and the like are also important considerations in selecting the best polymer for forming a pervaporation membrane.

The polynorbornene pervaporation membrane has a suitable separation factor (SF) for volatile organics, such as butanol, phenol or ethanol to provide an effective means to remove volatile organics, such as butanol, phenol or ethanol from a fermentation broth or from other waste as described herein. In one embodiment, the polynorbornene pervaporation membrane has a SF for volatile organics, such as butanol, phenol or ethanol of at least about 5. In another embodiment, the polynorbornene pervaporation membrane has a SF for volatile organics, such as butanol, phenol or ethanol of at least about 10. In yet another embodiment, the polynorbornene pervaporation membrane has a SF for volatile organics, such as butanol, phenol or ethanol of at least about 15. In still yet other embodiments, the polynorbornene pervaporation membrane has a SF for volatile organics, such as butanol, phenol or ethanol of at least about 20, at least about 25, or at least about 30. Moreover, any of the foregoing SFs can be achieved when the concentration of volatile organics, such as butanol, phenol or ethanol in a feed stream is 0.5% or higher, 1% or higher, 2% or higher, 3% or higher, or 4% or higher, or 5% or higher, or 6% or higher.

A suitable flux for volatile organics, such as butanol, phenol or ethanol can be achieved using polynorbornene pervaporation membranes of the present invention to provide an effective means to remove volatile organics, such as butanol, phenol or ethanol from a fermentation broth. In one embodiment, a flux for volatile organics, such as butanol, phenol or ethanol of at least about 100 g/m$^2$/hr can be achieved using such polynorbornene pervaporation membranes. In another embodiment, a flux for volatile organics, such as butanol, phenol or ethanol of at least about 150 g/m$^2$/hr can be achieved; in yet another embodiment, a flux for volatile organics, such as butanol, phenol or ethanol of at least about 200 g/m$^2$/hr can be achieved and in still another embodiment, a flux for volatile organics, such as butanol, phenol or ethanol of at least about 250 g/m$^2$/hr can be achieved using such polynorbornene pervaporation membranes. Furthermore, unlike what is generally found using previously known non-polynorbornene pervaporation membranes, any of the foregoing fluxes can be achieved when the concentration of volatile organics, such as butanol, phenol or ethanol in a feed stream is 0.5% or higher, 1% or higher, 2% or higher, 3% or higher, or 4% or higher, or 5% or higher, or 6% or higher.

It has been surprisingly found that various polycycloalkyl polynorbornenes polymers as described herein are suited for use in forming pervaporation membranes. It has been further observed that the vinyl addition polymerized polynorbornenes, particularly polymers derived from the repeat units of formulae (II) to (IV) in combination with repeat units of formula (V) are well suited for tailoring the resulting polymer's physical (e.g., glass transition temperature ($T_g$), modulus, free volume, hydrophobicity, hydrolytic stability, and the like) and pervaporation characteristics (e.g., SF and flux). Also, since polynorbornene polymers of this invention exhibit relatively high glass transition temperatures, the polymers of this invention can possibly offer the ability of operation as a pervaporation membrane at temperatures higher than possible for currently known membranes.

The following examples are detailed descriptions of methods of preparation and use of certain compounds/monomers, polymers and compositions of the present invention. The detailed preparations fall within the scope of, and serve to exemplify, the more generally described methods of preparation set forth above. The examples are presented for illustrative purposes only, and are not intended as a restriction on the scope of the invention. As used in the examples and throughout the specification the ratio of monomer to catalyst is based on a mole to mole basis.

EXAMPLES

Definitions thf or THF: tetrahydrofuran, CAS: [109-99-9];
DME: 1,2-dimethoxyethane, CAS: [110-71-4];
MeOH: methanol;
Tol: toluene;
EA: ethyl acetate;
DANFABA: N,N-dimethylaniliniumtetrakis-(pentafluorophenyl) borate;
RT: room temperature;
CPD: cyclopentadiene;
DCPD: dicyclopentadiene;
VAd: vinyl adamantane;
VNB: 5-vinylnorborn-2-ene or 5-vinylbicyclo[2.2.1]hept-2-ene, CAS: [3048-64-4];
VNBA: 2-vinylnorbornane or 2-vinylbicyclo[2.2.1]heptane, CAS: [2146-39-6];
VNBAPh: 2-phenyl-5-vinylnorbornane or 2-phenyl-5-vinylbicyclo[2.2.1]heptane;
VDDMN: 2-vinyldecahydro-1,4:5,8-dimethanonaphthalene;
NB: norbornene;
EtNB: 2-ethylnorborn-2-ene or 2-ethylbicyclo[2.2.1]hept-2-ene, CAS: [15403-89-1];
EtNBA: 2-ethylnorbornane or 2-ethylbicyclo[2.2.1]heptane, CAS: [2146-41-0];
TDNBA: tetracyclododecene norbornane;
NBNBA: 2-norbornenyl-5-norbornane or 2-(bicyclo[2.2.1]hept-5-en-2-yl)bicyclo[2.2.1]heptane;
HFANB: hydroxyhexafluoroisopropylmethyl norbornene or 2-(bicyclo[2.2.1]hept-5-en-2-ylmethyl)-1,1,1,3,3,3-hexafluoropropan-2-ol, CAS: [196314-61-1];
BuNB: 5-butylbicyclo[2.2.1]hept-2-ene, CAS: [22094-81-1];
NBNBAPh: 2-(bicyclo[2.2.1]hept-5-en-2-yl)-5-phenyl-bicyclo[2.2.1]heptane;
NBDDMN: 2-(bicyclo[2.2.1]hept-5-en-2-yl)decahydro-1,4:5,8-dimethanonaphthalene;
NB-Ad: 1-(bicyclo[2.2.1]hept-5-en-2-yl)adamantane;
NBCH$_2$OCH(CF$_3$)$_2$: 5-(((1,1,1,3,3,3-hexafluoropropan-2-yl)oxy)methyl)bicyclo[2.2.1]-hept-2-ene;
NBPh(CF$_3$)$_2$OH: 2-(4-(bicyclo[2.2.1]hept-5-en-2-yl)phenyl)-1,1,1,3,3,3-hexafluoropropan-2-ol;
PDMS: polydimethylsiloxanes;
PVDF: poly(vinylidene fluoride);
PAN: polyacrylonitrile;

PGMEA: propylene glycol methyl ether acetate CAS: [108-65-6];
GC: gas chromatography;
FID: flame ionization detector;
SEM: scanning electron microscopy;
Mw: molecular weight; and
PDI: polydispersity.

Generally the polymerization process includes the following. One or more norbornene monomers can be dissolved in one or more organic solvents and charged to a reactor vessel. Air is removed by sparging with nitrogen or an inert gas. A catalyst solution is added to the monomer solution. Using various techniques including extraction and the like a polynorbornene polymer is collected and dried.

Exemplary polymerization processes are described in published U.S. Patent Publication No. 20060020068 A1 at paragraphs [0053] and [0057], said paragraphs are herein incorporated by reference. Other exemplary polymerization processes are described in U.S. Pat. No. 5,468,819 and U.S. Patent Publication No. 20070066775, pertinent portions of which are also incorporated herein by reference.

Example 1

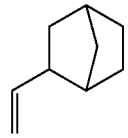

Endo, exo-isomeric
mixtures of
vinylnorbornane
(n-, x-VNBA)

Into an appropriate size and suitably equipped reaction vessel were placed endo-, exo-vinylnorbornene (n-, x-VNB) (4007 g, 33.3 mol), methanol (4000 mL methanol, 253 g 0.5% Pd on alumina spheres (Escat™ 16 catalyst (BASF)), and calcium oxide (23.6 g). The reaction mixture was stirred while being flushed 3 times with nitrogen and stirring was stopped intermittently while flushing the reactor three times with hydrogen. Then the stirring was set at 276 rpm and temperature was maintained at 14° C. as the reactor was charged with 105 psi hydrogen. The hydrogen was consumed by the reaction as indicated by the pressure drop and the reactor was recharged with hydrogen. During the course of the reaction, the temperature was maintained around 14° C. by cooling, since the hydrogenation reaction is exothermic. The reaction was continually monitored by GC by taking aliquots of the reaction mixture. After about 7 hours the GC analysis showed 0.4% VNB, 27% exo-VNBA, 69% endo-VNBA, 1.8% EtNBA, and 1.8% total of three vinyl-norbornane isomers. The reactor was drained to collect ~8 L of material which was filtered through Celite® filter aid with supplemental methanol rinsing. From the resulting 10 L liquid, a lower VNBA-enriched phase of ~2 L separated and was removed.

The remainder was washed with 2.5 gallons brine. The clear aqueous phase was separated from the lower organic and emulsion phases and then mixed with the previously separated 2 L of VNBA-enriched phase and with the 4 L methanol used to rinse the reactor. Another 1 gal brine was added. After mixing, the phases were separated to collect ~6 L organic phase. The organic phases were combined, dried over sodium sulfate and filtered to give 3709 g (91% yield) of 94.5% endo-, exo-VNBA containing 0.4% VNB, 2.7% EtNBA, and 2.4% total of two vinylnorbornane isomers.

The aqueous phase (~20 L) was extracted with 1 L pentane, dried over sodium sulfate, and rotary evaporated to obtain 107.3 g of 93.7% endo-, exo-VNBA containing 0.3% VNB, 2.9% EtNBA, and 3.0% total of two vinylnorbornane isomers. This was combined with the previous neat material to give 3816 g for 94% yield.

The Celite filter aid was extracted with pentane to recover 18.6 g containing 0.2% VNB, 65.4% endo-, exo-VNBA, 3.8% EtNBA, and 40.5% total of two vinylnorbornane isomers.

GC analysis was performed on a DB5-MS column, 25 m, 0.32 mm ID, 0.52 μm film. Gradient: Hold at 45° C. for 11 min, then heat to 300° C. at 40° C./min, hold 4 min at 300° C. Injector: 275° C. Detector: 350° C. (FID). Retention times: 5.237 min (VNB), 6.679 (exo-VNBA), 7.075 minutes (endo-VNBA), 7.211 min (EtNBA), 8.127 & 8.288 minutes (VNBA isomers).

Example 2

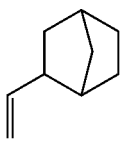

Exo-vinylnorbornane
(x-VNBA)

Into an appropriate size and suitably equipped reaction vessel were placed exo-vinylnorbornene (x-VNB) (100 g, 0.832 mol), methanol (100 ml), 0.5% Pd on alumina spheres (6.33 g, Escat 16), and calcium oxide (0.59 g). The hydrogenation reaction was carried out substantially following the procedures as set forth in Example 1 by pressurizing with hydrogen several times as the pressure dropped after each pressurization with hydrogen. The reaction temperature was maintained around room temperature and was continually monitored by GC. The reaction was stopped when the GC analyses showed 0-0.15% VNB, 0.5% EtNB, 92.5-93.1% exo-VNBA, 4% EtNBA, 2% total of three vinylnorbornane isomers, and 0.7% VNB impurity. The material was filtered through Celite® and rinsed with methanol. To the resulting milky liquid was added 500 mL brine. A yellow upper phase separated and was collected to give 87.2 g product. Sodium chloride (10 g) was added to the remaining aqueous phase and then sonicated while heating to about 50° C. Another 6.92 g organic phase separated. This was combined with the previous organic phase, dried over sodium sulfate, and filtered to give 88.65 g (87% yield) of 91.6% exo-VNBA containing 0.4% EtNB, 4.8% EtNBA, 2.6% total of three vinylnorbornane isomers, and 0.6% VNB impurity.

GC analysis was performed on a DB5 column, 30 m, 0.25 mm ID, 0.25 μm film. Gradient: Hold at 45° C. for 10 min, then heat to 120° C. at 15° C./min and then heat to 300° C. at 40° C./min, hold 2 min at 300° C. Injector: 200° C. Detector: 350° C. (FID). Retention times: 7.590 min (VNB), 7.953 min (EtNB), 9.758 (exo-VNBA), 9.876 min (EtNBA), 10.791, 10.957, & 11.090 minutes (VNBA isomers), 15.565 min (VNB impurity).

Example 3

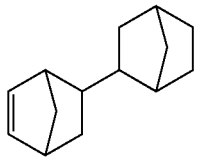

Endo-, exo-isomeric mixtures of
2-(bicyclo[2.2.1]hept-5-en-2-yl)
bicyclo[2.2.1]heptane
(n, x-NBNBA)

Into an appropriate size and suitably equipped reactor were placed endo-, exo-vinylnorbornane (n, x-VNBA) (2100 grams, 17.18 mol). Melted dicyclopentadiene (DCPD, 288 grams, 2.18 mol) was mixed with 32 grams of n, x-VNBA into a 2000 mL Schott bottle. The Schott bottle was then placed on a balance so that the delivery weight could be monitored. The meter feed line was flushed with the DCPD/VNBA mixture and then affixed and sealed into the entry port of the reactor. The sealed reactor was flushed three times with nitrogen and then finally sealed with 5 psig nitrogen pressure. The mixture was stirred at 300 rpm while heating the reaction mixture to 220° C. When the temperature had stabilized at 220° C., the DCPD/VNBA feed was initiated at 1.39 mL/min. The metered feed was completed in 4 hours. Maximum pressure obtained was 76 psig. The mixture was cooled to 25° C. and drained from the reactor to collect 2380 grams crude product. GC analysis showed approximately 0.2% cyclopentadiene (CPD), 0.06% vinylnorbornene (VNB), 63.2% VNBA, 2.4% ethylnorbornane (EtNBA), 3.3% (VNBA) isomers, 0.6% DCPD, 25% endo-, exo-NBNBA, 0.2% CPD trimer, and 4.7% tetracyclododecene norbornane (TDNBA). The above charge was repeated twice. Total crude material (6956 grams) of endo-,exo-2-(bicyclo[2.2.1]hept-5-en-2-yl)bicyclo[2.2.1]heptane was combined into a 12 L three neck, round bottom flask and purified through two 12 inch glass column sections with stainless steel wire gauze packing. The vacuum distillation conditions were 70-76° C. and 0.9-1.4 torr. The distillation cuts (57% yield) contained approximately 0.1% VNBA, 0.04% DCPD, 99.25% endo-, exo-NBNBA, and 0.28% CPD trimer as clear, colorless liquids.

GC analysis was performed on an Ultra 1 Methyl Siloxane column, 25 m, 0.20 mm ID, 0.33 μm film. Gradient: Hold at 70° C. for 1 min, then heat to 240° C. at 10° C./min, hold 10 min at 240° C. Injector: 200° C. Detector: 250° C. (FID). Retention times: 1.6 min (CPD), 3.8 min (VNB), 4.5-4.68 min (VNBA), 4.71 min (EtNBA), 4.78-5.08 min (VNBA isomers), 5.7-6.0 min (DCPD), 12.1-12.25 min (endo-, exo-NBNBA), 13.2-14.3 min (CPD trimer), and 18.5-19 min (TDNBA).

Example 4

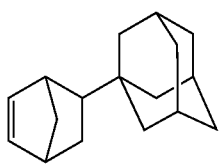

1-(bicyclo[2.2.1]hept-5-en-2-
yl)adamantane (NB-Ad)

Into a suitable high pressure tube reactor were placed various stoichiometric molar ratios of vinyl admantane: cyclopentadiene (VAd:CPD) at 4:1, 6:1, and 8:1 and heated in a hot oil bath maintained at 220° C. The batch high pressure tube reactions were run for 2 and 4 hours. At the end of the reaction, the high pressure tubes were removed from the bath and quenched in a wet ice bath. The resultant crude monomer samples were analyzed by GC. Each of the reaction mixture produced about 2-4% NB-Ad.

GC analysis was performed on an Ultra 1 Methyl Siloxane column, 25 m, 0.20 mm ID, 0.33 μm film. Gradient: Hold at 70° C. for 1 min, then heat to 240° C. at 10° C./min, hold 10 min at 240° C. Injector: 200° C. Detector: 250° C. (FID). Retention times: 1.78 min (CPD), 6.3-6.5 min (DCPD), 10-10.3 min (VAd), 10.35-10.4 min (VAd isomers), 13.2-14.3 min (CPD trimer), 17.8-17.9 min (NB-Ad), 19-22 min (CPD tetramer).

Example 5

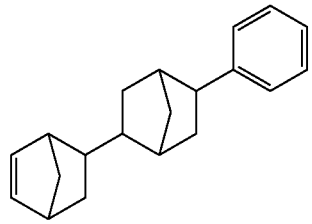

2-(bicyclo[2.2.1]hept-5-en-2-yl)-5-phenyl-
bicyclo[2.2.1]heptane (NBNBAPh)

Example 3 is substantially repeated except for using VNBAPh in place of VNBA to obtain the title compound.

Example 6

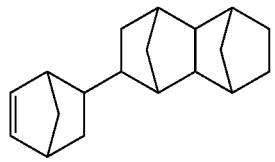

2-(bicyclo[2.2.1]hept-5-en-2-
yl)decahydro-1,4:5,8-
dimethanonaphthalene (NBDDMN)

Example 3 is substantially repeated except for using VDDMN in place of VNBA to obtain the title compound.

Example 7

NBNBA/HFANB Copolymer

NBNBA (2.04 g, 0.011 mol) and HFANB (2.96 g, 0.011 mol) were dissolved in a mixture of toluene and ethyl acetate (95/5) and then charged to a suitably sized reactor vessel. The vessel and solution were sparged with nitrogen for 30 min to remove any air. DANFABA (0.0026 mmol) was added to the monomer solution in a dry-box. The solution was heated to 70° C. and stirred for 30 min in order to ensure complete dissolution of DANFABA. A Pd catalyst solution was prepared in a dry-box by dissolving 0.0104 g Pd1206 (0.0086 mmol) in 0.2 g anhydrous toluene and ethyl acetate (95/5) mixture. The catalyst solution was injected to the monomer solution using a syringe. The monomer to catalyst ratio was kept at 2500:1. The reaction mixture was stirred for 16 hours with oil bath controlled at 70° C. The reaction mixture was diluted by adding 20 g tetrahydrofuran. The polymer was then precipitated by slowly adding the reaction mixture to MeOH and filtered. The white polymer powder was collected and dried in a vacuum oven at 100° C. overnight. GC was used to determine the monomer conversion as well as monomer composition in the resulting polymer. The polymer composition was determined to be NBNBA/HFANB (64/36). Molecular weight of the polymer was 300,000 with PDI of 2.3.

Examples 8-14

Various Compositions of NBNBA/HFANB Copolymers

Example 7 was substantially repeated in these Examples except for employing a solvent mixture containing different ratios of toluene (Tol) and ethyl acetate (EA). Also, in Examples 8 and 9, 0.5 weight percent of tributyl silane was used as a chain transfer agent (CTA). The reaction was run for a period of 16 hours in Examples 8 to 13, and in Example 14, the reaction was carried out for a period of 72 hours. The solvent mixture, CTA, the rate of conversion of NBNBA/HFANB, the composition of monomers in the resulting copolymers, $M_w$ and PDI are summarized in Table 1, n.m. stands for not measured.

$NBCH_2OCH(CF_3)_2$ monomer was employed instead of HFANB to obtain 50/50 copolymer of NBNBA/$NBCH_2OCH(CF_3)_2$.

Example 17

Various Compositions of NBNBA/BuNB Copolymers

Example 7 was substantially repeated except that appropriate amounts of BuNB monomer were employed instead of HFANB to obtain copolymers of NBNBA/BuNB containing various different molar ratios of 90/10, 80/20, 70/30, 60/40 and 50/50. In these examples solvent mixture containing different ratios of cyclohexane and EA (95/5, 90/10 and 85/15) by volume were employed depending upon the copolymer that was prepared. The weight average molecular weight, $M_w$, of the polymers thus obtained was in the range of 300,000 to 400,000 with a PDI of about 2.

Example 18

NBNBA/NB Copolymer

Example 7 was substantially repeated except that appropriate amounts of NB monomer were employed instead of HFANB to obtain a copolymer of NBNBA/NB having a molar ratio of 90/10. The polymerization solvent employed in this case was a mixture of cyclohexane and EA in the ratio of 85/15 by volume.

TABLE 1

Various Compositions of NBNBA/HFANB Copolymers

| | Conditions | | | | | |
|---|---|---|---|---|---|---|
| Ex. No. | Reaction Time, hrs. | Solvent Tol/EA | CTA (%) | NBNBA/HFANB % Conversion | Composition NBNBA/HFANB | $M_w$/PDI |
| 8 | 16 | 100/0 | 0.5 | 96/52 | 65/35 | n.m. |
| 9 | 16 | 100/0 | 0.5 | n.m. | n.m. | 190,000/3.3 |
| 10 | 16 | 100/0 | 0 | n.m. | n.m. | 251,000/4.3 |
| 11 | 16 | 95/5 | 0 | 100/58 | 64/36 | 300,000/2.3 |
| 12 | 16 | 90/10 | 0 | 97/55 | 64/36 | 246,000/2.3 |
| 13 | 16 | 80/20 | 0 | 93/50 | 66/34 | 215,000/2.3 |
| 14 | 72 | 95/5 | 0 | 100/75 | 58/42 | n.m. |

Example 15

$NBNBA/NBPhC(CF_3)_2OH$ Copolymer

Example 7 was substantially repeated except that appropriate amounts of $NBPhC(CF_3)_2OH$ monomer was employed instead of HFANB to obtain 50/50 copolymer of $NBNBA/NBPhC(CF_3)_2OH$. Molecular weight of the polymer was 266,000 with a PDI of 4.4.

Example 16

$NBNBA/NBCH_2OCH(CF_3)_2$ Copolymer

Example 7 was substantially repeated except that appropriate amounts of

Example 19

NBNBA Homopolymer

Example 7 was substantially repeated except that only NBNBA monomer was employed in this Example 19 to obtain homopolymer of NBNBA. The polymerization solvent employed in this case was a mixture of cyclohexane and EA in the ratio of 85/15 by volume.

Example 20

NBNBAPh/HFANB Copolymer

Example 7 is substantially repeated except that appropriate amounts of NBNBAPh monomer are employed instead of NBNBA to obtain a copolymer of NBNBAPh/HFANB.

Example 21

NBDDMN/HFANB Copolymer

Example 7 is substantially repeated except that appropriate amounts of NBDDMN monomer are employed instead of NBNBA to obtain a copolymer of NBDDMN/HFANB.

Example 22

NB-Ad/HFANB Copolymer

Example 7 is substantially repeated except that appropriate amounts of NB-Ad monomer are employed instead of NBNBA to obtain a copolymer of NB-Ad/HFANB.

Example 23

NBNBA ROMP Polymer

Toluene was degassed, stirred over sodium benzophenone ketyl, and vacuum transferred prior to use. NBANB and trimethylphosphine (PMe$_3$) were degassed and vacuum transferred from sodium. All chemicals used during the polymer synthesis were stored and handled in a dry-box under nitrogen atmosphere. The Schrock-type initiator 2,6-diisopropylphenylimido(neophylidene) molybdenum(VI) bis(tert-butoxide) (28 mg, 0.051 mmol) was dissolved in toluene and added to a round bottom flask. PMe$_3$ (19 mg, 0.26 mmol) was added to the flask to attenuate the polymerization rate. NBANB (4.76 g, 0.025 mol) was then added, corresponding to an initial monomer concentration of 4 weight percent. The flask was sealed and the reaction mixture was stirred at room temperature for 75 min. The polymerization was terminated with benzaldehyde (0.54 g, 0.0051 mol) and stirred for 30 minutes. The polymer was recovered by precipitation into excess methanol. The initiator was removed by repeatedly dissolving the polymer in toluene and precipitating into excess methanol. The resulting white polymer was isolated by filtration and dried under vacuum at room temperature. The molecular weight was determined by gel permeation chromatography (GPC) equipped with a differential refractive index detector calibrated with narrow-distribution polystyrene standards. The polystyrene-equivalent number average molecular weight was 150,000 g/mol with a PDI of 1.11. The glass transition temperature (T$_g$) of the polymer was measured using differential scanning calorimetry (DSC) using a heating and cooling rate of 10° C./min. The T$_g$ was determined from the second heating ramp to be 150° C.

Example 24

Hydrogenation Product of ROMP Polymer of NBNBA

Dry polymer (3.95 g) from Example 23 was dissolved in 1.5 L cyclohexane and added to a 2 L pressure vessel. Palladium supported on calcium carbonate (12.5 g, 5 wt % Pd) was added and the vessel was sealed and purged with nitrogen followed by hydrogen. The vessel was charged with 400 psi hydrogen, heated to 100° C., and stirred for 14.5 hours. The hydrogenation reaction was monitored by Fourier transform infrared (FTIR) spectroscopy. The catalyst was removed by filtration, and the polymer was recovered by precipitation into excess methanol. The polymer was isolated by filtration and dried in a vacuum oven at 145° C. for 3 hours. GPC analysis showed no evidence of degradation during hydrogenation. DSC of the hydrogenated polymer showed a T$_g$ of 116° C.

Example 25

NBDDMN ROMP Polymer

Example 23 was essentially repeated in this Example 25 except for employing appropriate amounts of the monomer, NBDDMN, and the first generation Grubbs initiator, bis(tricyclohexylphosphine)benzylidene ruthenium(IV) dichloride in toluene at room temperature. The polymerization was terminated with excess ethyl vinyl ether. The polymer was isolated by precipitation into methanol followed by filtration. The T$_g$ of the dried polymer was measured to be 201° C. by DSC.

Example 26

Hydrogenation Product of ROMP Polymer of NBDDMN

Example 24 was essentially repeated except for using the ring-opened poly(NBDDMN) obtained from Example 25 and was hydrogenated with palladium supported on calcium carbonate (5 wt % Pd) in cyclohexane under 400 psi hydrogen. The hydrogenation reaction proceeded at 100° C. for 22 hours. The T$_g$ of the hydrogenated polymer was 165° C. as measured by DSC.

It should be noted that the method of forming polymers as set forth in Example 7 to Example 26 are not the only methods for making such polymers. Also, it should be noted that such polymers were not the only polymers evaluated. Thus the polymer embodiments in accordance with the present invention can also be prepared by addition or ROMP polymerization of the appropriate monomers as described hereinabove in the presence of a single or multi-component Group VIII transition metal catalyst/initiator or other appropriate catalysts/initiators preformed in an appropriate solvent.

Example 27

Preparation of a Membrane

Single Thickness Film or a Thin Film Composite (TFC) membrane: A polymer formed in accordance with this invention, for instance as specifically disclosed in any one of the Examples 7 to 26, is dissolved in an organic solvent to make a solution which is then filtered. After filtration, trapped gas is removed. The polymer is poured onto a substrate and pulled to form a film, dried and ready for use. In some cases, the film is dried and can be removed from the substrate and used as unsupported film.

Specifically, polymer formed in Example 7 (10 g) was dissolved in THF (100 g) to make a solution which was filtered through a 5 micron nylon filter. After filtration, the solution was allowed to roll overnight on a jar roller to remove trapped gas introduced during the filtration. The polymer solution was poured onto a PAN ultrafiltration substrate and pulled, using a Gardner Film Casting Knife to form a film having an essentially uniform thickness. The film was allowed to dry in the air for one hour followed by annealing at 60° C. for 10 min to form the TFC membrane. In parallel, the film was coated on a glass substrate and the thickness was measured using Dektak profilometer.

Double Thickness Film: Double thickness films are prepared in a similar manner to the single film except that a second layer of the solution is provided over the first film before the first film is removed from substrate, and then pulling the second film. After the second pass is pulled, the double film is dried and then removed from the substrate and ready for use.

For example, the single thickness film example described above is followed, except that about 5 hours after the first film casting, a second layer is provided by pouring a second aliquot of the polymer solution over the first film and pulling it as was done above with a Gardner Film Casting Knife. After the second pass is pulled, the film is dried in the air overnight.

Example 28

Pervaporation Test

The membrane was cut into 2 inch circles for installation into a capsule that was then placed in the pervaporation testing device. The charge liquid in the testing device was heated to desired temperature circulating in by-pass mode and then circulated through the membrane housing at 80 mL/min in the continuous mode to check for any leaks. After this check was completed a vacuum was pulled on the dry side of the membrane and any permeate was collected into a cooled trap (cooled with liquid nitrogen). The system was allowed to run for three hours, collected permeate was warmed to room temperature and evaluated.

Evaluation of the Permeate

The room temperature permeate collected as described above, having separated into a two-phase liquid, was weighed and found to be 2.2 g. To this permeate, 0.4 g MeOH was added to make the phases miscible, thus providing a single phase permeate. The single phase permeate (1 gram) was added to a GC sampling vial containing 0.02 g PGMEA and mixed thoroughly. A sample from the vial was then injected into a Gas Chromatograph where the % butanol or % phenol was determined by evaluating the area of the butanol or phenol peak with respect to the PGMEA standard.

In addition to forming a flat sheet membrane supported on PAN ultrafiltration substrate, the possibility of forming hollow fibers that encompass the polynorbornenes of embodiments of the present invention is evaluated. The following procedure is used to successfully form hollow fibers for further evaluation.

Example 29

Hollow Fiber Membrane Film Making

A polymer formed in accordance with this invention, for instance as specifically disclosed in any one of the Examples 7 to 26, is dissolved in an organic solvent and filtered to remove particles. This solution is then pressure transferred through the outer bore of a spinneret while a mixture of a solvent and salt is simultaneously pressure transferred through the inner bore of the spinneret. These pressure transferred materials are directed to a precipitating bath to provide hollow fibers. The dimensions of the hollow fibers can be controlled by the size of the inner/outer bores and the pressures under which the solutions are transferred.

For example, a copolymer of Example 7, NBNBA/HFANB (64/36) is dissolved in THF at 10 wt % and filtered through a 100 micron filter to remove particles. This solution is then pressure transferred through the outer bore of a double-bore spinneret having an outside diameter of 1.0 mm and an inside diameter of 0.5 mm while a mixture of 20/80 MeOH/5 wt. % LiCl (aq.) solution is simultaneously pressure transferred through the inner bore of the spinneret. These pressure transferred materials are directed to a precipitating bath (20/80 MeOH/water) where hollow fibers are observed and evaluated. The dimensions of the hollow fibers removed from the bath can be confirmed by SEM.

Example 30

Forming Thin Film Composite Hollow Fibers

Generally speaking, a polymer formed in accordance with this invention, for instance as specifically disclosed in any one of the Examples 7 to 26, is dissolved in a suitable solvent (e.g., THF) at a suitable concentration (e.g., 10 wt. %) and filtered through a 100 micron filter to remove particles. A hollow fiber microfiltration or ultrafiltration membrane (e.g., 0.1 micron PVDF or 3000 MWCO polysulfone) with the inner lumen blocked off is dipped into the polynorbornene solution and then pulled out of the solution. The solvent is removed by drying the fiber at suitable conditions (e.g., 23-60° C. for 0.5-12 h). The dimensions of the hollow fibers removed from the bath can be confirmed by SEM.

Example 31

Comparative Operability of Single Thickness Films Made from Different Polynorbornene Compositions and Polymers of this Invention A comparison of polymers of this invention and various other polynorbornene compositions was performed to observe selective separation performance of n-butanol in a pervaporation test. The two dependant variables that were examined were flux and percent organics in the permeate. The feed solution concentration was varied (1% or 2%). A heat bath was used to heat the feed solution to 65° C. Through heat loss, this gives a housing temperature of about 60° C. In order to collect the permeate samples vacuum traps in liquid nitrogen were used. The vacuum was 0.4 in Hg (10 Torr). The feed solution was pumped into the system by a diaphragm pump at 70 mL/min. A three hour test was used to collect samples. A polymer, 50/50 NBNBA/HFANB copolymer prepared in accordance with Example 7, was compared with a 50/50 copolymer of BuNB/HFANB, both used as unsupported thin film composite membrane prepared in accordance with procedures as described in Example 26. The thicknesses of the films were varied and were from about 0.7 microns to about 10 microns, and the effective diameter is 43.5 mm. In the following Tables 2 to 4, BuNB stands for 5-butyl-2-norbornene, HFANB stands for hydroxyhexafluoroisopropylmethyl norbornene and NBNBA stands for 2-norbornenyl-5-norbornane.

TABLE 2

Pervaporation Performance with 1% n-butanol feed

| Membrane Sample No. | Polymer (monomer ratio) | Film Thickness (μm) | BuOH in Permeate (%) | Flux (g/m²h) |
|---|---|---|---|---|
| 1 | BuNB/HFANB (50/50) | 0.7 | 17 | 2160 |
| 2 | | 10 | 19 | 230 |
| 3 | NBNBA/HFANB† (50/50) | 0.7 | 27 | 2500 |
| 4 | | 2.5 | 31 | 840 |
| 5 | NBNBA/HFANB† (50/50) | 2.5 | 25 | 1000 |
| 6 | NBNBA/HFANB† (50/50) | 2.5 | 28 | 810 |

†Polymers from different batches

It is quite apparent from Table 2 that the membrane Sample Nos. 3 to 6 made from 50:50 copolymer of NBNBA/HFANB, i.e., the polymers of this invention generally exhibit much superior separation performance than the membrane Sample Nos. 1 and 2 formed from 50:50 copolymer of BuNB/HFANB. It is important to note that much higher concentration of n-butanol in the permeate was achieved using NBNBA/HFANB polymer of this invention at or about the same or higher flux when compared with similar thickness of films formed form BuNB/HFANB copolymer. Generally, flux is directly proportional to the thickness of the film, and thus thinner the membrane higher the flux. For example, as summarized in Table 2, Sample 2, a 10 μm thick membrane formed from 50:50 copolymer of BuNB/HFANB exhibited almost similar separation characteristics as that of a 0.7 μm thickness film (Sample No. 1), i.e., about 17 to 19% butanol in the permeate while the flux reduced from 2160 g/m² h to 230 g/m² h, i.e., about ten times lower flux. Whereas membranes formed from 50:50 copolymer of NBNBA/HFANB exhibited a significant improvement in both flux and percent butanol in the permeate at film thickness of 0.7 (Sample No. 3) and 2.5 μm (Sample Nos. 4, 5 and 6), almost a 65% improvement over BuNB/HFANB copolymer.

Table 3 summarizes results obtained for 2% n-butanol feed.

TABLE 3

Pervaporation Performance with 2% n-butanol feed

| Membrane Sample No. | Polymer | Film Thickness (μm) | BuOH in Permeate (%) | Flux (g/m²h) |
|---|---|---|---|---|
| 7 | BuNB/HFANB (50/50) | 0.7 | 34 | 3320 |
| 8 | NBNBA/HFANB (50/50) | 2.5 | 50 | 1500 |

Table 4 summarizes results obtained for 2% phenol feed. The 2% phenol feed was prepared to mimic the "green phenol" mother solution.

TABLE 4

Pervaporation Performance with 2% phenol feed

| Membrane Sample No. | Polymer | Film Thickness (μm) | Phenol in Permeate (%) | Flux (g/m²h) |
|---|---|---|---|---|
| 9 | BuNB/HFANB (50/50) | 0.7 | 5 | 1500 |
| 10 | NBNBA/HFANB (50/50) | 2.5 | 14 | 830 |

It is evident from the results presented in Tables 2 to 4, the membranes of the instant invention provide much superior separation performance when compared with BuNB/HFANB copolymer.

Example 32

SF and Flux for Various Butanol Concentrations

Separation factor (SF) and flux were measured for various butanol concentrations in water at 60° C. with a membrane made from NBNBA/HFANB copolymer having a $M_w$ of 200,000-300,000. The results are shown in FIGS. 3 to 6. The feed was heated to 65° C. and charged at 70 mL/min while applying a vacuum of 0.4 in Hg to the apparatus. Membrane film thickness was 3 microns.

Figure 3:
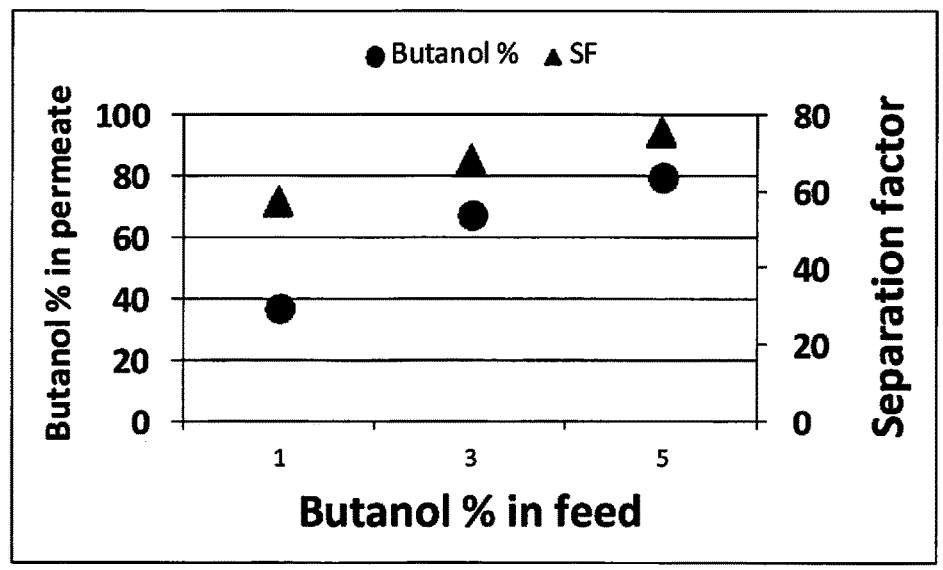
FIGS. 3 and 5 show the relationship between separation factor (SF) and various concentrations of the organics in the feed, butanol or phenol, respectively, for embodiments in accordance with the present invention. Also shown in FIGS. 3 and 5, respectively, are the relationship between percent butanol or phenol in the permeate vs. percent butanol or phenol in the feed.
Figure 5:
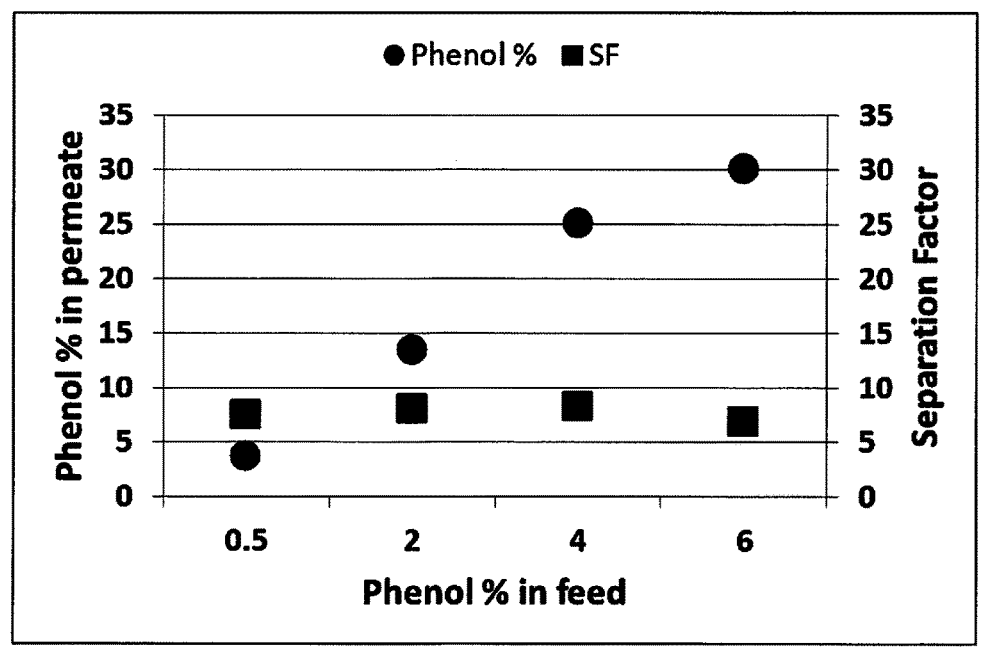

FIG. 3 shows the increased SF achieved with increased concentrations of butanol, see right y-axis. Also shown in FIG. 3 plotted on the left y-axis is the percent butanol in the permeate. The percent butanol in the permeate increased with increase in butanol concentration in the feed. It is remarkable to note that the 80 percent butanol in the permeate can be achieved when the butanol in the feed is increased to 5 percent. FIG. 5 shows similar results observed for phenol. Again, phenol shows a good SF for the studied range of concentration of phenol in the feed from 0.5% to 6%. But interestingly, the percent phenol in the permeate continually increases with increase in phenol concentration in the feed.

Figure 4:
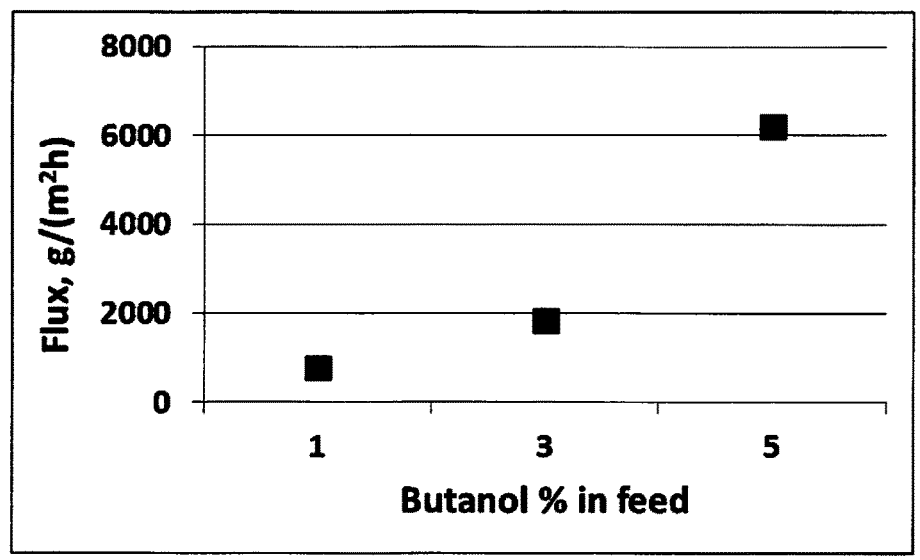
FIGS. 4 and 6 show the relationship between flux and percent butanol or phenol in the feed for embodiments in accordance with the present invention.
Figure 6:
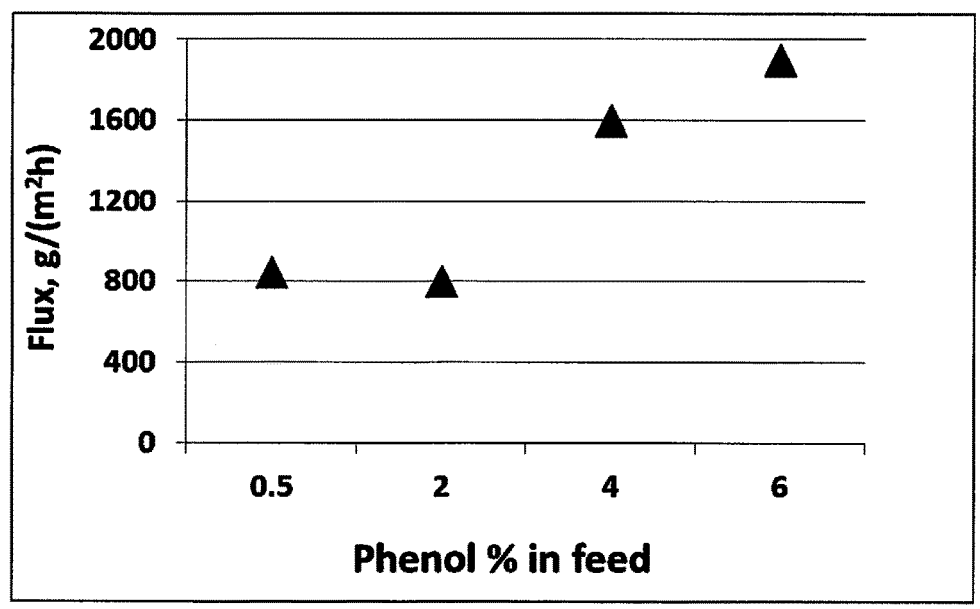

FIG. 4 reports the increased flux achieved with increased concentrations of butanol, another interesting result, as shown by the curve with a positive slope. A similar result was obtained for phenol as depicted in FIG. 6.

Example 33

Effect of pH on Phenol Separation from Phenol Feed

Figure 7:
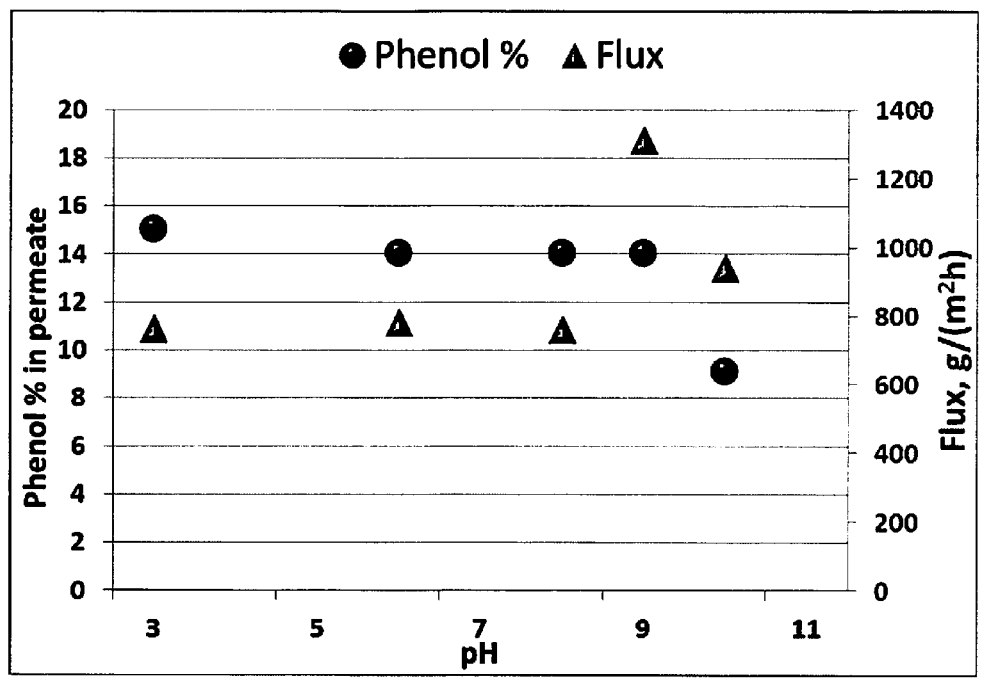
FIG. 7 shows the relationship between pH and percent phenol in the permeate as well as the relationship between pH and flux of a feed containing phenol for embodiments in accordance with the present invention.

The effect of pH on phenol separation from the phenol feed was also investigated using a membrane formed from NBNBA/HFANB copolymer. The results are shown in FIG. 7. The feed was heated to 65° C. and charged at 70 mL/min while applying a vacuum of 0.4 in Hg to the apparatus. Membrane film thickness was 3 microns. FIG. 7 shows that generally pH has no effect on flux especially at lower to neutral pH, but some increase in flux was observed at about pH of 9 or higher. The percent phenol in the permeate also remained same at lower to neutral pH. As the pH increased to about 10, the phenol concentration dropped. These studies demonstrate the utility of the membranes of this invention at various pH ranges.

Example 34

Operability Experiment of Thin Film Composite Membrane for Various Isomeric Butanols A comparison of isomeric alcohols was performed to observe performance of iso-butanol and n-butanol in a pervaporation test. The dependent variables that were examined are flux, separation factor and percent isomeric butanol in the permeate. Varying concentrations of the feed solution (about 1% and 3% for n-butanol and about 3% and 6.7% for isobutanol) are used in each test to examine the affects of concentration. Two different temperatures were used in two separate experiments; a heat bath was used to heat the feed solution in the first experiment to about 40° C. and in the second experiment to about 65° C. Through heat loss, this gives a housing temperature of about 37° C. or 60° C. respectively. In order to collect the permeate samples vacuum traps in liquid nitrogen were used. The vacuum was 0.4 in Hg. The feed solution was pumped into the system by a diaphragm pump at 70 mL/min. For feed concentrations of 3% or greater a three hour test was used to collect samples. Lower concentrations required more time to collect enough sample to analyze. The polymer film was a NBNBA/HFANB copolymer made in accordance with Example 7. These were used as supported thin films. The average thickness of the films was about 3 microns and the effective diameter was 43.5 mm. The data are summarized in Tables 5 and 6.

TABLE 5

(Isobutanol)

| | | |
|---|---|---|
| Feed Concentration, % | 3 | 6.7 |
| Temp. (° C.) | 60 | 60 |
| Flux, g/(m² · h) | 1850 | 6875 |
| SF | 36 | 45 |
| Isobutanol in permeate, % | 53 | 76 |

TABLE 6

(n-Butanol)

| | | | |
|---|---|---|---|
| Feed Concentration % | 1 | 3 | 3 |
| Temp. (° C.) | 37 | 60 | 37 |
| Flux, g/(m² · h) | 370 | 1827 | 915 |
| SF | 54 | 75 | 69 |
| n-butanol in permeate, % | 36 | 70 | 68 |

Example 35

Pervaporation Performance of Various Compositions of NBNBA/HFANB Copolymers

Example 32 was substantially repeated with the exception of forming a single film membrane using polymers formed from Examples 8-14. In all of these runs the pervaporation was carried out at 60° C. The performance of these films in the pervaporation of 1% n-butanol feed is summarized in Table 7. It is evident from these results that all of the films formed from the polymers of Examples 8-14 exhibit excellent pervaporation properties in separating n-butanol from 1% n-butanol feed.

TABLE 7

| Polymer Used | n-BuOH in permeate (%) | Flux (g/m²h) | Film Thickness (μm) |
|---|---|---|---|
| Example 8 | 28 | 1050 | 2 |
| Example 9 | 36 | 765 | 2.5 |
| Example 10 | 32 | 1140 | 2 |
| Example 11 | 34 | 1200 | 2 |
| Example 12 | 36 | 1140 | 2 |

TABLE 7-continued

| Polymer Used | n-BuOH in permeate (%) | Flux (g/m²h) | Film Thickness (μm) |
|---|---|---|---|
| Example 13 | 37 | 711 | 3 |
| Example 14 | 35 | 760 | 2.5 |

Example 36

Pervaporation Performance of NBNBA/HFANB Copolymer with Phenol Feed

Example 32 was substantially repeated with the exception of using a phenol feed of varying concentrations. The pervaporation membrane was made with a copolymer of NBNBA/HFANB made in accordance with Example 7. The results are summarized in Table 8.

TABLE 8

| Temp. (° C.) | Feed (%) | Film Thickness (μm) | Flux (g/m²h) | Phenol in Permeate (%) | SF |
|---|---|---|---|---|---|
| 25 | 2 | 3 | 68 | 12 | 6.6 |
| 70 | 2 | 2.5 | 964 | 12 | 6.4 |
| 60 | 0.5 | 2.5 | 850 | 3.6 | 7.4 |
| 60 | 2 | 2.5 | 1313 | 15 | 7.9 |
| 60 | 4 | 2.5 | 1600 | 25.5 | 8.2 |
| 60 | 6 | 2.5 | 1916 | 30.6 | 6.9 |
| 60 | 8 | 2.5 | 2556 | 47 | 10.1 |

Example 37

Pervaporation Performance of NBNBA Homopolymer with Phenol Feed

Example 32 was substantially repeated with the exception of using a phenol feed of varying concentrations. The pervaporation membrane was made with a homopolymer of NBNBA made in accordance with Example 19. The results are summarized in Table 9.

TABLE 9

| Temp. (° C.) | Feed (%) | Film Thickness (μm) | Vacuum (Torr) | Flux (g/m²h) | Phenol in Permeate (%) | SF |
|---|---|---|---|---|---|---|
| 37 | 2 | 2.5 | 0.5 | 3600 | 8.3 | 4.4 |
| 37 | 2 | 2.5 | 1 | 1792 | 12.5 | 6.8 |
| 37 | 2 | 2.5 | 3.2 | 1192 | 24.3 | 15.5 |
| 37 | 2 | 2.5 | 10 | 949 | 22.0 | 13.6 |
| 37 | 2 | 2.5 | 20 | 272 | 21.1 | 12.8 |
| 60 | 8 | 2.5 | 0.5 | 2514 | 36.5 | 6.6 |
| 60 | 8 | 2.5 | 1 | 3071 | 46.0 | 9.8 |
| 60 | 8 | 2.5 | 3.2 | 2017 | 54.3 | 13.6 |
| 60 | 8 | 2.5 | 10 | 1647 | 50.4 | 11.6 |
| 60 | 8 | 2.5 | 20 | 1510 | 20.6 | 3.0 |

Example 38

Pervaporation Performance of NBNBA/BuNB and NBNBA/NB Copolymers with Phenol Feed Example 32 was substantially repeated with the exception of using 2% phenol feed and membrane made from copolymers of various compositions made in accordance with respective Examples as summarized in Table 10. All pervaporation runs were made at 10 torr vacuum and at a temperature of 60° C. The results are summarized in Table 10.

TABLE 10

| Example No. | Polymer composition (mole ratio) | Flux (g/m²h) | Phenol in Permeate (%) |
|---|---|---|---|
| 18 | NBNBA/NB (90/10) | 750 | 20 |
| 17 | NBNBA/BuNB (90/10) | 490 | 22 |
| 17 | NBNBA/BuNB (80/20) | 470 | 22 |
| 17 | NBNBA/BuNB (70/30) | 440 | 22 |

Example 39

Pervaporation Performance of Phenol Feed Containing Salts

Example 32 was substantially repeated with the exception of using a 2 weight percent phenol feed containing various concentration of salts and employing membranes formed from different polymers as described herein. The results are summarized in Table 11. All of the experiments were carried out at a temperature of 60° C., 10 torr vacuum and run for 2 hours. In each of these experiments the percent phenol in the permeate was respectively 18.5% for 50:50 NBNBA/HFANB copolymer membrane and 20% for NBNBA homopolymer membrane as well as 80:20 NBNBA/BuNB copolymer membrane.

TABLE 11

| Ionic Species | | Permeate Concentration (ppm) | | |
|---|---|---|---|---|
| In the Feed | | NBNBA/HFANB | NBNBA | NBNBA/BuNB |
| Ion | Level (ppm) | (50:50) (Example No. 7) | homopolymer (Ex. No. 19) | (80:20) (Ex. No. 17) |
| Na+ | 5170 | 21 | 30 | 17 |
| K+ | 740 | 1.6 | 1.9 | 0.7 |
| NH₄⁺ | 2000 | 2066 | 1182 | 3538 |
| PO₄³⁻ | 870 | <0.1 | 0.3 | 0.4 |
| SO₄²⁻ | 5000 | <0.1 | 1.9 | 0.1 |
| CH₃CO₂⁻ | 76 | 0.5 | 3.4 | 0.2 |

Finally it should be noted that while the evaluations of the polynorbornene materials presented herein focus on butanol and phenol laced charge liquids, it is anticipated that polynorbornene materials will be found to be selective to other organic materials found in other aqueous charge liquids or fermentation broths, or selective to non-polar materials in polar organic materials.

While the invention has been explained in relation to certain embodiments, it is to be understood that various modifications thereof will become apparent to those skilled in the art upon reading the specification. Therefore, it is to be understood that the invention disclosed herein is intended to cover such modifications as fall within the scope of the appended claims.

What is claimed is:

1. A compound of formula (I):

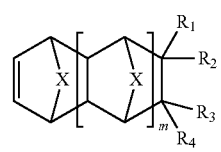

(I)

wherein:
each occurrence of X independently represents —CH₂— or —CH₂—CH₂—;
m is an integer from 0 to 5 inclusive;
at least one of $R_1$, $R_2$, $R_3$ and $R_4$ independently represents -L-($C_7$-$C_{14}$)tricycloalkyl or a group of formula (A):

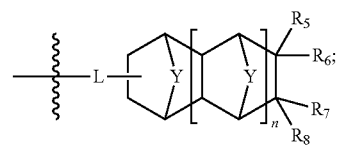

(A)

wherein:
each occurrence of Y independently represents —CH₂— or —CH₂—CH₂—;
n is 1; and
$R_5$, $R_6$, $R_7$ and $R_8$ independently represents hydrogen, methyl, ethyl, linear or branched ($C_3$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, ($C_5$-$C_{10}$)heteroaryl, ($C_5$-$C_{10}$)heteroaryl($C_1$-$C_3$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy, ($C_1$-$C_6$)acyloxy, or halogen;
L represents a bond; or
$R_1$ and $R_3$ taken together with the carbon atom to which they are attached form a substituted or unsubstituted ($C_5$-$C_7$)cycloalkyl or ($C_6$-$C_{12}$)bicycloalkyl ring;
remaining one or more of $R_1$, $R_2$, $R_3$ and $R_4$ independently represents hydrogen, methyl, ethyl, linear or branched ($C_3$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_6$-$C_{10}$)aryl($C_1$-$C_3$)alkyl, ($C_5$-$C_{10}$)heteroaryl, ($C_5$-$C_{10}$)heteroaryl($C_1$-$C_3$)alkyl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$))aryloxy($C_1$-$C_3$)alkyl, ($C_5$-$C_{10}$)heteroaryloxy($C_1$-$C_3$)alkyl, ($C_6$-$C_{10}$)aryloxy, ($C_5$-$C_{10}$)heteroaryloxy, ($C_1$-$C_6$)acyloxy, or halogen;
wherein each of aforementioned groups, where valence is permissible, is optionally substituted with one or more groups selected from ($C_1$-$C_6$)alkyl, ($C_3$-$C_7$)cycloalkyl, ($C_1$-$C_6$)perfluoroalkyl, halogen, hydroxy, acetoxy, phenyl, hydroxyphenyl, acetoxyphenyl and a group of formula (B):

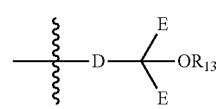

(B)

wherein:
D is $(CH_2)_r$ where r is an integer from 1 to 5 inclusive, phenylene, $C_6H_4(CH_2)_s$ where s is an integer from 1 to 3 inclusive, or $((CH_2)_t-O)_u$ where t and u independently are integers from 1 to 4 inclusive;
E is methyl, ethyl, $CF_3$ or $C_2F_5$; and
$R_{13}$ is hydrogen or $(C_1-C_5)$alkyl.

2. The compound according to claim 1, wherein X is $CH_2$, m is 0;
each of $R_2$, $R_3$ and $R_4$ is hydrogen, $R_1$ being a group of formula (A),
wherein Y is $CH_2$, n is 1, and is represented by formula (II):

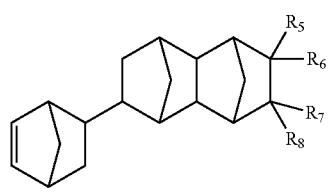

(II)

wherein:
each occurrence of $R_5$, $R_6$, $R_7$ and $R_8$ independently represents hydrogen, methyl, ethyl, -n-propyl, iso-propyl, n-butyl, iso-butyl, sec-butyl, tert-butyl, $CF_3$, phenyl, benzyl, hydroxy, acetoxy, methoxy, ethoxy, n-propoxy, iso-propoxy, n-butoxy, iso-butoxy, tert-butoxy, PhOH, PhOAc, $C(CF_3)_2OH$, $CH_2C(CF_3)_2OH$, $(CH_2)_2C(CF_3)_2OH$, $(CH_2)_3C(CF_3)_2OH$, or $PhC(CF_3)_2OH$.

3. The compound according to claim 1, which is selected from the group consisting of:
2-(bicyclo[2.2.1]hept-5-en-2-yl)bicyclo[2.2.1]heptane;
2-(bicyclo[2.2.1]hept-5-en-2-yl)-5-phenyl-bicyclo[2.2.1]heptane;
2-(bicyclo[2.2.1]hept-5-en-2-yl)decahydro-1,4:5,8-dimethanonaphthalene;
2-(bicyclo[2.2.1]heptenyl)-6-bicyclo[2.2.1]heptylbicyclo[2.2.1]heptane;
3-(bicyclo[2.2.1]hept-5-en-2-yl)tricyclo[2.2.1.0$_{2,6}$]heptane; and
1-(bicyclo[2.2.1]hept-5-en-2-yl)adamantane.

4. A compound of formula (III):

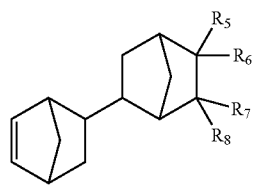

(III)

wherein:
each occurrence of $R_5$, $R_6$, $R_7$ and $R_8$ independently represents hydrogen, methyl, n-propyl, iso-propyl, n-butyl, iso-butyl, sec-butyl, tert-butyl, $CF_3$, bicycloheptyl, or phenyl.

5. The compound according to claim 4, which is selected from the group consisting of:

2-(bicyclo[2.2.1]hept-5-en-2-yl)bicyclo[2.2.1]heptane;
2-(bicyclo[2.2.1]hept-5-en-2-yl)-5-phenyl-bicyclo[2.2.1]heptane; and
2-(bicyclo[2.2.1]heptenyl)-6-bicyclo[2.2.1]heptylbicyclo[2.2.1]heptane.

6. A polymer comprising a first repeating unit represented by formula (IA), said repeating unit is derived from a monomer of formula (I):

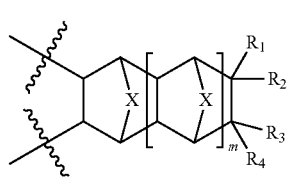

(IA)

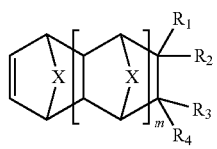

(I)

wherein:
each occurrence of X independently represents —$CH_2$— or —$CH_2$—$CH_2$—;
m is an integer from 0 to 5 inclusive;
at least one of $R_1$, $R_2$, $R_3$ and $R_4$ independently represents a group of formula (A):

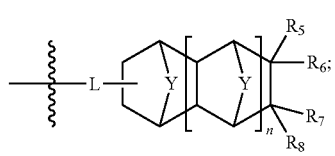

(A)

wherein:
each occurrence of Y independently represents —$CH_2$— or —$CH_2$—$CH_2$—;
n is 0 or 1; and
$R_5$, $R_6$, $R_7$ and $R_8$ independently represents hydrogen, methyl, ethyl, linear or branched $(C_3-C_{12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_5-C_{10})$heteroaryl, $(C_5-C_{10})$heteroaryl$(C_1-C_3)$alkyl, hydroxy, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl, $(C_5-C_{10})$heteroaryloxy$(C_1-C_3)$alkyl, $(C_6-C_{10})$aryloxy, $(C_5-C_{10})$heteroaryloxy, $(C_1-C_6)$acyloxy, or halogen;
L represents a bond; or
$R_1$ and $R_3$ taken together with the carbon atom to which they are attached form a substituted or unsubstituted $(C_5-C_7)$cycloalkyl or $(C_6-C_{12})$bicycloalkyl ring;
remaining one or more of $R_1$, $R_2$, $R_3$ and $R_4$ independently represents hydrogen, methyl, ethyl, linear or branched $(C_3-C_{3-12})$alkyl, $(C_3-C_{12})$cycloalkyl, $(C_6-C_{12})$bicycloalkyl, $(C_7-C_{14})$tricycloalkyl, $(C_6-C_{10})$aryl, $(C_6-C_{10})$aryl$(C_1-C_3)$alkyl, $(C_5-C_{10})$heteroaryl, $(C_5-C_{10})$heteroaryl$(C_1-C_3)$alkyl, hydroxy, $(C_1-C_{12})$alkoxy, $(C_3-C_{12})$cycloalkoxy, $(C_6-C_{12})$bicycloalkoxy, $(C_7-C_{14})$tricycloalkoxy, $(C_6-C_{10})$aryloxy$(C_1-C_3)$alkyl, $(C_5-C_{10})$ heteroaryloxy($C_1$-$C_3$)alkyl, ($C_6$-$C_{10}$)aryloxy, ($C_5$-$C_{10}$) heteroaryloxy, ($C_1$-$C_6$)acyloxy, or halogen;

wherein each of aforementioned groups, where valence is permissible, is optionally substituted with one or more groups selected from ($C_1$-$C_6$)alkyl, ($C_3$-$C_7$)cycloalkyl, ($C_1$-$C_6$)perfluoroalkyl, halogen, hydroxy, acetoxy, phenyl, hydroxyphenyl, acetoxyphenyl and a group of formula (B):

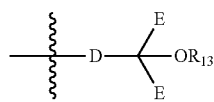
(B)

wherein:
D is $(CH_2)_r$ where r is an integer from 1 to 5 inclusive, phenylene, $C_6H_4(CH_2)_s$ where s is an integer from 1 to 3 inclusive, or $((CH_2)_t-O)_u$ where t and u independently are integers from 1 to 4 inclusive;
E is methyl, ethyl, $CF_3$ or $C_2F_5$; and
$R_{13}$ is hydrogen or ($C_1$-$C_5$)alkyl.

7. The polymer according to claim 6, wherein $R_1$ is a group of formula (A), $R_5$ is hydrogen or phenyl, X and Y are $CH_2$, m is 0, n is 0 or 1, L is a bond, and $R_2$, $R_3$, $R_4$, $R_6$, $R_7$ and $R_8$ are each hydrogen.

8. The polymer according to claim 6 further comprising a second repeating unit represented by formula (VA), said second repeat unit is derived from the monomer of formula (V):

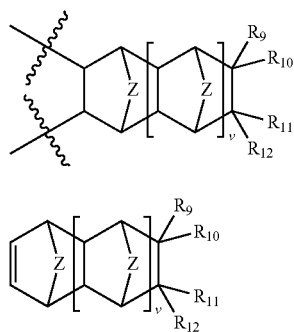

wherein:
each occurrence of Z independently represents —$CH_2$— or —$CH_2$—$CH_2$—;
v is an integer from 0 to 5 inclusive;
$R_9$, $R_{10}$, $R_{11}$ and $R_{12}$ independently represents hydrogen, methyl, ethyl, linear or branched ($C_3$-$C_{12}$)alkyl, ($C_3$-$C_{12}$)cycloalkyl, ($C_6$-$C_{12}$)bicycloalkyl, ($C_7$-$C_{14}$)tricycloalkyl, ($C_6$-$C_{10}$)aryl, ($C_5$-$C_{10}$)heteroaryl, hydroxy, ($C_1$-$C_{12}$)alkoxy, ($C_3$-$C_{12}$)cycloalkoxy, ($C_6$-$C_{12}$)bicycloalkoxy, ($C_7$-$C_{14}$)tricycloalkoxy, ($C_6$-$C_{10}$)aryloxy, ($C_5$-$C_{10}$)heteroaryloxy, ($C_1$-$C_6$)acyloxy, halogen, or a group of formula (B):

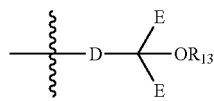
(B)

wherein:
D is $(CH_2)_r$ where r is an integer from 1 to 5 inclusive, phenylene, $C_6H_4(CH_2)_s$ where s is an integer from 1 to 3 inclusive, or $((CH_2)_t-O)_u$ where t and u independently are integers from 1 to 4 inclusive;
E is methyl, ethyl, $CF_3$ or $C_2F_5$; and
$R_{13}$ is hydrogen or ($C_{1-5}$)alkyl; and wherein each of aforementioned groups, where valence is permissible, is optionally substituted with a group selected from ($C_1$-$C_6$)alkyl, ($C_3$-$C_7$)cycloalkyl, ($C_6$-$C_{12}$)bicycloalkyl, ($C_7$-$C_{14}$)tricycloalkyl, ($C_6$-$C_{10}$)aryl, ($C_1$-$C_6$)perfluoroalkyl, halogen, hydroxy, acetoxy, phenyl, hydroxyphenyl, acetoxyphenyl and a group of formula (B):

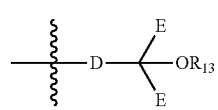
(B)

wherein D, E and $R_{13}$ are as defined above.

9. The polymer according to claim 8, wherein Z is —$CH_2$—, v is 0, each of $R_{10}$, $R_{11}$ and $R_{12}$ is hydrogen and $R_9$ is —$CH_2C(CF_3)_2OH$, $R_1$ is a group of formula (A), X and Y are —$CH_2$—, m is 0, n is 0 or 1, $R_5$ is hydrogen or phenyl, each of $R_2$, $R_3$, $R_4$, $R_6$, $R_7$ and $R_8$ is hydrogen.

10. The polymer according to claim 6, which is a homopolymer of 2-(bicyclo [2.2.1]hept-5-en-2-yl)bicyclo[2.2.1]-heptane.

11. The polymer according to claim 8 which is selected from:
a copolymer of 2-(bicyclo[2.2.1]hept-5-en-2-yl)bicyclo [2.2.1]heptane and hydroxyhexafluoroisopropylmethylnorbornene;
a copolymer of 2-(bicyclo[2.2.1]hept-5-en-2-yl)bicyclo [2.2.1]heptane and norbornene; and
a copolymer of 2-(bicyclo[2.2.1]hept-5-en-2-yl)bicyclo [2.2.1]heptane and 5-n-butylbicyclo[2.2.1]hept-2-ene.

12. A compound of formula (I):

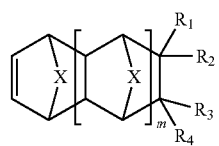
(I)

wherein:
each occurrence of X independently represents —$CH_2$— or —$CH_2$—$CH_2$—;
m is an integer from 0 to 5 inclusive;
at least one of $R_1$, $R_2$, $R_3$ and $R_4$ independently a group of formula (A):

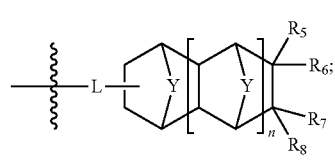
(A)

wherein:
each occurrence of Y independently represents —CH$_2$— or —CH$_2$—CH$_2$—;
n is 0; and
R$_5$, R$_6$, R$_7$ and R$_8$ independently represents hydrogen, methyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, (C$_5$-C$_{10}$)heteroaryl, (C$_5$-C$_{10}$)heteroaryl(C$_1$-C$_3$)alkyl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy(C$_1$-C$_3$)alkyl, (C$_5$-C$_{10}$)heteroaryloxy(C$_1$-C$_3$)alkyl, (C$_6$-C$_{10}$)aryloxy, (C$_5$-C$_{10}$)heteroaryloxy, (C$_1$-C$_6$)acyloxy, or halogen;
L represents a bond; or
R$_1$ and R$_3$ taken together with the carbon atom to which they are attached form a substituted or unsubstituted (C$_5$-C$_7$)cycloalkyl or (C$_6$-C$_{12}$)bicycloalkyl ring;
remaining one or more of R$_1$, R$_2$, R$_3$ and R$_4$ independently represents hydrogen, methyl, ethyl, linear or branched (C$_3$-C$_{12}$)alkyl, (C$_3$-C$_{12}$)cycloalkyl, (C$_6$-C$_{12}$)bicycloalkyl, (C$_7$-C$_{14}$)tricycloalkyl, (C$_6$-C$_{10}$)aryl, (C$_6$-C$_{10}$)aryl(C$_1$-C$_3$)alkyl, (C$_5$-C$_{10}$)heteroaryl, (C$_5$-C$_{10}$)heteroaryl(C$_1$-C$_3$)alkyl, hydroxy, (C$_1$-C$_{12}$)alkoxy, (C$_3$-C$_{12}$)cycloalkoxy, (C$_6$-C$_{12}$)bicycloalkoxy, (C$_7$-C$_{14}$)tricycloalkoxy, (C$_6$-C$_{10}$)aryloxy(C$_1$-C$_3$)alkyl, (C$_5$-C$_{10}$)heteroaryloxy(C$_1$-C$_3$)alkyl, (C$_6$-C$_{10}$)aryloxy, (C$_5$-C$_{10}$)heteroaryloxy, (C$_1$-C$_6$)acyloxy, or halogen;
wherein each of aforementioned groups, where valence is permissible, is optionally substituted with one or more groups selected from (C$_1$-C$_6$)alkyl, (C$_3$-C$_7$)cycloalkyl, (C$_1$-C$_6$)perfluoroalkyl, halogen, hydroxy, acetoxy, phenyl, hydroxyphenyl, acetoxyphenyl and a group of formula (B):

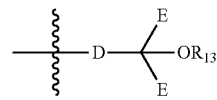

(B)

wherein:
D is (CH$_2$)$_r$ where r is an integer from 1 to 5 inclusive, phenylene,
C$_6$H$_4$(CH$_2$)$_s$ where s is an integer from 1 to 3 inclusive, or ((CH$_2$)$_t$—O)$_u$ where t and u independently are integers from 1 to 4 inclusive;
E is methyl, ethyl, CF$_3$ or C$_2$F$_5$; and
R$_{13}$ is hydrogen or (C$_1$-C$_5$)alkyl.

13. The compound according to claim 12, wherein X is CH$_2$, m is 0; each of R$_2$, R$_3$ and R$_4$ is hydrogen, R$_1$ being a group of formula (A), wherein Y is CH$_2$, n is 0, L is a bond, and is represented by formula (III):

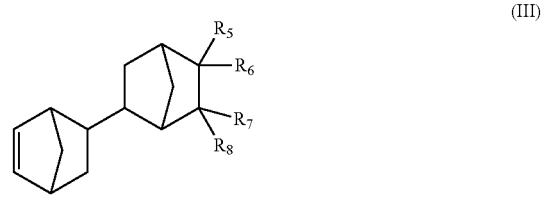

(III)

wherein:
each occurrence of R$_5$, R$_6$, R$_7$ and R$_8$ independently represents hydrogen, methyl, n-propyl, iso-propyl, n-butyl, iso-butyl, sec-butyl, tert-butyl, CF$_3$, bicycloheptyl, phenyl, benzyl, hydroxy, acetoxy, methoxy, ethoxy, n-propoxy, iso-propoxy, n-butoxy, iso-butoxy, tert-butoxy, PhOH, PhOAc, C(CF$_3$)$_2$OH, CH$_2$C(CF$_3$)$_2$OH, (CH$_2$)$_2$C(CF$_3$)$_2$OH (CH$_2$)$_3$C(CF$_3$)$_2$OH, or PhC(CF$_3$)$_2$OH.

* * * * *